US006956042B2

(12) United States Patent
Bhatti et al.

(10) Patent No.: US 6,956,042 B2
(45) Date of Patent: Oct. 18, 2005

(54) N-ARYL DIAZASPIRACYCLIC COMPOUNDS AND METHODS OF PREPARATION AND USE THEREOF

(75) Inventors: Balwinder S. Bhatti, Winston-Salem, NC (US); Craig Harrison Miller, Winston-Salem, NC (US); Jeffrey Daniel Schmitt, Winston-Salem, NC (US)

(73) Assignee: Targacept, Inc., Winston-Salem, NC (US)

( * ) Notice: Subject to any disclaimer, the term of this patent is extended or adjusted under 35 U.S.C. 154(b) by 0 days.

(21) Appl. No.: 10/607,930

(22) Filed: Jun. 27, 2003

(65) Prior Publication Data

US 2004/0067930 A1 Apr. 8, 2004

Related U.S. Application Data

(60) Provisional application No. 60/394,337, filed on Jul. 5, 2002.

(51) Int. Cl.$^7$ ..................... A61K 31/438; C07D 221/20
(52) U.S. Cl. ...................... 514/278; 514/299; 566/15; 566/113; 566/268.1
(58) Field of Search ...................... 546/15, 113, 268.1; 514/278, 299

(56) References Cited

U.S. PATENT DOCUMENTS

| | | | |
|---|---|---|---|
| 3,282,947 A | 11/1966 | Grogan et al. | 260/293 |
| 4,665,079 A * | 5/1987 | Culbertson et al. | 514/312 |
| 4,922,901 A | 5/1990 | Brooks et al. | 128/203.26 |
| 5,187,166 A | 2/1993 | Kikuchi et al. | 514/249 |
| 5,583,140 A | 12/1996 | Bencherif et al. | 514/299 |
| 5,597,919 A | 1/1997 | Dull et al. | 544/242 |
| 5,604,231 A | 2/1997 | Smith et al. | 514/256 |
| 5,616,716 A | 4/1997 | Dull et al. | 546/300 |
| 5,663,356 A | 9/1997 | Ruecroft et al. | 546/300 |
| 5,672,601 A | 9/1997 | Cignarella | 514/249 |
| 5,733,912 A | 3/1998 | Wasicak et al. | 514/253 |
| 5,852,041 A | 12/1998 | Cosford et al. | 514/351 |
| 6,022,868 A | 2/2000 | Olesen et al. | 514/210 |
| 2003/0092700 A1 | 5/2003 | Czollner et al. | 514/217.01 |
| 2003/0171359 A1 | 9/2003 | Dahmann et al. | |

FOREIGN PATENT DOCUMENTS

| | | |
|---|---|---|
| EP | 0 297 858 | 1/1989 |
| EP | 0 360 390 | 3/1990 |
| EP | 0 417 631 | 3/1991 |
| EP | 0 970 957 A1 | 1/2000 |
| GB | 2 142 332 A | 1/1985 |
| GB | 2 295 387 | 5/1996 |
| WO | WO 94/08992 | 4/1994 |
| WO | WO 96/31475 | 10/1996 |
| WO | WO 96/40682 | 12/1996 |
| WO | WO 97/40049 | 10/1997 |
| WO | WO 98/25619 | 6/1998 |
| WO | WO 99/21834 | 5/1999 |
| WO | WO 01/30780 A3 | 5/2001 |
| WO | WO 01/30780 A2 | 5/2001 |
| WO | WO 01/66545 A1 | 9/2001 |

OTHER PUBLICATIONS

Mukund, M. M., et al., "Spirocyclic Nonpeptide Gycoprotein IIb–IIIa Antagonists. Part 3: Synthesis and SAR of Potent and Specific 2,8–Diazaspiro[4.5]decanes," *Biorganic & Medicinal Chemistry Letters*, 12(7): 1103–1107 (2002).

Smyth, M.S., et al., "Spirocyclic Nonpeptide Glycoprotein Iib–IIIa Antagonists. Part 1: Design of Potent and Specific 3,9–Diazaspiro [5.5]undecanes," *Bioorganic & Medicinal Chemistry Letters*, 11(10): 1289–1292 (2001).

Partial International Search Report (Nov. 7, 2003).

Mullen, G., et al., "(—)–Spiro[1–azabicyclo[2.2.2]octane3, 5'–oxazolidin–2'–one], a Conformationally Restricted Analogue of Acetylcholine, Is a Highly Selective Full Agonist at the α7 Nicotinic Acetylcholine Receptor," *J. Med. Chem.*, 43(22): 4045–4050 (2000).

International Search Report (Apr. 6, 2004).

Abramovitch, R.A., editor, "Pyridine and Its Derivatives," Supp. Part Three, pp. 3–5, in *Chemistry of Heterocyclic Compounds*, vol. 14 (Interscience Publishers, 1974).

Adamcik, J.A., and E.J. Miklasiewicz, "Cyanoethylation. I. Weakly Basic Catalysts in the Reaction of Acrylonitrile with Active Methylene Compounds," *J. Org. Chem.* 28: 336–339 (1963).

Arneric, S., et al., "Preclinical Pharmacology of ABT–418: A Prototypical Cholinergic Channel Activator for the Potential Treatment of Alzheimer's Disease," *CNS Drug Rev.*, 1(1): 1–26 (1995).

(Continued)

*Primary Examiner*—Rita Desai
(74) *Attorney, Agent, or Firm*—Womble Carlyle Sandridge & Rice, PLLC

(57) ABSTRACT

Compounds, pharmaceutical compositions including the compounds, and methods of preparation and use thereof are disclosed. The compounds are N-aryl diazaspirocyclic compounds, bridged analogs of N-heteroaryl diazaspirocyclic compounds, or prodrugs or metabolites of these compounds. The aryl group can be a five- or six-membered heterocyclic ring (heteroaryl). The compounds and compositions can be used to treat and/or prevent a wide variety of conditions or disorders, particularly those disorders characterized by dysfunction of nicotinic cholinergic neurotransmission, including disorders involving neuromodulation of neurotransmitter release, such as dopamine release. CNS disorders, which are characterized by an alteration in normal neurotransmitter release, are another example of disorders that can be treated and/or prevented. The compounds and compositions can also be used to alleviate pain. The compounds can: (i) alter the number of nicotinic cholinergic receptors of the brain of the patient, (ii) exhibit neuroprotective effects and (iii) when employed in effective amounts, not result in appreciable adverse side effects (e.g., side effects such as significant increases in blood pressure and heart rate, significant negative effects upon the gastro-intestinal tract, and significant effects upon skeletal muscle).

7 Claims, No Drawings

OTHER PUBLICATIONS

Arneric, S.P., et al., "Cholinergic channel modulators as a novel therapeutic strategy for Alzheimer's disease," *Exp. Opin. Invest. Drugs*, 5(1): 79–100 (1996).

Bannon, A.W., et al., "Broad–Spectrum, Non–Opioid Analgesic Activity by Selective Modulation of Neuronal Nicotinic Acetylcholine Receptors," *Science*, 279: 77–81 (1998).

Bencherif, M., et al., "RJR–2403: A Nicotinic Agonist with CNS Selectivity I: In Vitro Characterization," *J. Pharmacol. Exper. Therapeutics*, 279(3): 1413–1421 (1996).

Berkowitz, D.B., and M.K. Smith, "Enantiomerically Enriched α–Methyl Amino Acids. Use of an Acyclic, Chiral Alanine–Derived Dianion with a High Diastereofacial Bias," *J. Org. Chem.*, 60: 1233–1238 (1995).

Brioni, J.D., et al., "The Pharmacology of (–)–Nicotine and Novel Cholinergic Channel Modulators," *Adv. Pharmacol.*, 37: 153–215 (1997).

Burger, A., et al., "Some Derivatives of Tetrahydropyran as Potential Pharmacodynamic Agents," *J. Am. Chem. Soc.*, 72: 5512–5515 (1950).

Cheng, Y., and W.H. Prusoff, "Relationship Between the Inhibition Constant ($K_1$) and the Concentration of Inhibitor which Causes 50 Per Cent inhibition ($I_{\_}$) of an Enzymatic Reaction," *Biochem. Pharmacol.* 22(23): 3099–3108 (1973).

Chiari, A., et al., "Sex Differences in Cholinergic Analgesia I: A Supplemental Nicotinic Mechanism in Normal Females," *Anesthesiology* 91(5): 1447–1454 (1999).

Ciblat, S., et al., "A new route to 2–spiropiperidines," *Tet. Lett.*, 42: 4815–4817 (2001).

Clarke, K., and K. Rothwell, "A Kinetic Study of the Effect of Substituents on the Rate of Formation of Alkylpyridinium Halides in Nitromethane Solution," *J. Chem. Soc.*, 1885–1895 (1960).

Comins, D.L, adn M.O. Killpack, "Lithiation of Methoxy-pyridines Directed by α–Amino Alkoxides," *J. Org. Chem.*, 55(1): 69–73 (1990).

Cosford, N.D.P., et al., "(S)–(–) 5–Ethynyl–3–(1–methyl–2–pyrrolidinyl) pyridine Maleate (SIB–1508Y): A Novel Anti–Parkinsonian Agent with Selectivity for Neuronal Nicotinic Acetylcholine Receptors," *J. Med. Chem.*, 39(17) : 3235–3237 (1996).

Culbertson, T.P., et al., "Quinolone Antibacterial Agents Substituted at the 7–Position with Spiroamines. Synthesis and Structure–Activity Relationships," *J. Med. Chem.*, 33(8): 2270–2275 (1990).

Damaj, M.I., et al., "Analgesic Activity of Metanicotine, A Selective Nicotinic Agonist," *Society for Neuroscience*, 23: 669 ABSTRACT 266.9 (1997).

Damaj, M.I., et al., "Antinociceptive and Pharmacological Effects of Metanicotine, a Selective Nicotinic Agonist," *J. Pharmacol. Exp. Ther.*, 291(1): 390–398 (1999).

Decina, P., et al., "Cigarette Smoking and Neuroleptic–Induced Parkinsonism," *Biol. Psychiatry*, 28(6): 502–508 (1990).

Elliott, J.M., et al., "Serine Derived $NK_1$ Antagonists 2: A Pharmacophore Model for Arylsulfonamide Binding," *Bioorg. Med. Chem. Lett.*, 8: 1851–1856 (1998).

Fornicola, R.S., et al., "A New Synthesis of α–Amino Acid Derivatives Employing Methyl Nitroacetate as a Versatile Glycine Template," *J. Org. Chem.*, 63(11): 3528–3529 (1998).

Genin, M.J., et al., "Synthesis and Crystal Structure of a Peptidomimetic Containing the (R)–4.4–Spiro Lactam Type–II β–Turn Mimic," *J. Org. Chem.*, 58(8): 2334–2237 (1993).

Genin, M.J., and R.L. Johnson, "Design, Synthesis, and Conformational Analysis of a Novel Spiro–Bicyclic System as a Type II β–Turn Peptidomimetic," *J. Amer. Chem. Soc.*, 114(23): 8778–8783 (1992).

Gibson, S., et al., "Principal Components Describing Biological Activities and Molecular Diversity of Heterocyclic Aromatic Ring Fragments," *J. Med. Chem.*, 39(20): 4065–4072 (1996).

Grogan, C.H., et al. "Spiranes. VII. Neuroleptics Derived from Azaspiranes," *J. Med. Chem.*, 8: 62–73 (1965).

Hall, G.H., and D.M. Turner, "Effects of Nicotine on the Release of $^3H$–Noradrenaline from the Hypothalamus," *Biochemical Pharmacology*, 21: 1829–1838 (1972).

Hamon, M., "Neuropharmacology of anxiety: perspectives and prospects," *TiPS*, 15: 36–39 (1994).

Hansch, C., et al., "The Parabolic Dependence of Drug Action upon Lipophilic Character as Revealed by a Study of Hypnotics," *J. Med. Chem.*, 11(1): 1–11 (1967).

Hansch, C., et al., "A Survey of Hammett Substituent Constants and Resonance and Field Parameters," *Chem. Rev.*, 91(2): 165–195 (1991).

Hansen, M.M., et al., "An Enantioselective Synthesis of Cis Perhydroisoquinoline LY235959," *J. Org. Chem.*, 63(3): 775–785 (1998).

Harsing, Jr., L.G., et al., "Dopamine Efflux from Striatum After Chronic Nicotine: Evidence for Autoreceptor Desensitization," *J. Neurochem.*, 59(1): 48–54 (1992).

Hartwig, J.F., et al., "Room–Temperature Palladium–Catalyzed Amination of Aryl Bromides and Chlorides and Extended Scope of Aromatic C—N Bond Formation with a Commercial Ligand," *J. Org. Chem.*, 64(15): 5575–5580 (1999).

Hertog, H.J.D., et al., "The Directive Influence of the N–Oxide Group During the Nitration of Derivatives of Pyridine N–Oxide (IV) [1]) Nitration of 3–bromo–5methoxy– and 3,5–dimethoxy–pyridine–N–oxide[2])," *Recueil Trav. Chim. Pays–Bas*, 74(8/9): 1171–1179 (1955).

Hery, F., et al., "Control of the Release of Newly Synthetized $^3H$–5–Hydroxytryptamine by Nicotinic and Muscarinic Receptors in Rat Hypothalamic Slices," *Naunyn–Schmiedeberg's Arch. Pharmacol.*, 296: 91–97 (1977).

Hinds, M.G., et al., "Synthesis, Conformational Properties, and Antibody Recognition of Peptides Containing β–Turn Mimetics Based on α–Alkylproline Derivatives," *J. Med. Chem.*, 34(6): 1777–1789 (1991).

Hoffman, J.M., et al., "Synthesis and Evaluation of 2–Pyridinone Derivatives as HIV–1–Specific Reverse Transcriptase Inhibitors. 4. 3–[2–(Benzoxazol–2–yl)ethyl]–5–ethyl–6–methylpyridin–2(1H)–one and Analogues," *J. Med. Chem.*, 36(8): 953–966 (1993).

Holladay, M.W., et al., "Neuronal Nicotinic Acetylcholine Receptors as Targets for Drug Discovery," *J. Med. Chem*, 40(26): 4169–4194 (1997).

Holland, A. et al., "Isothiazoles. Part IX. Isothiazolopyrimidines," *J. Chem. Soc.*, 7277–7282 (1965).

Hughes, D.L., "The Mitsunobu Reaction," *Org. React.*, 42: 335–657 (1992).

Hughes, D.L., "Progress in the Mitsunobu Reaction. A Review," *Org. Prep. Proced. Int.*, 28(1): 129–164 (1996).

Islam, A.M., and R.A. Raphael, "A Direct Transformation of cycloHexanones into bicyclo [5:3:0] Dec–7–en–9–ones," *J. Chem. Soc.*, 3151–3154 (1955).

Kim, K., et al., "Novel Bicyclic Lactams as XaaPro Type VIβ Turn Mimics: Design, Synthesis and Evaluation," *J. Org. Chem.*, 61(9): 3138–3144 (1996).

Lall, M.S., et al., "Serine and Threonine β–Lactones: A New Class of Hepatitis A Virus 3C Cysteine Proteinase Inhibitors," *J. Org. Chem.*, 67(5): 1536–1547 (2002).

Latli, B., et al., "Novel and Potent 6–Chloro–3–pyridinyl Ligands for the α4β2 Neuronal Nicotnic Acetylcholine Receptor," *J. Med. Chem.*, 42(12): 2227–2234 (1999).

Lavand'homme, P., and J.C. Eisenach, "Sex Differences in Cholinergic Analgesia II: Differing Mechanisms in Two Models of Allodynia," *Anesthesiology*, 91(5): 1455–1461 (1999).

Lippiello, P.M., et al., "RJR–2403: A Nicotinic Agonist with CNS Selectivity II. In Vivo Characterization," *J. P. E. T.*, 279(3): 1422–1429 (1996).

Majer, Z., et al., "Synthesis and Absolute Configuration of 1,7 Diazaspiro[4,4]Nonane–2,6–Dione," *Coll. Czech. Chem. Comm.*, 47(3): 950–960 (1982).

Old, D.W., et al., "A Highly Active Catalyst for Palladium–Catalyzed Cross–Coupling Reactions: Room–Temperature Suzuki Couplings and Amination of Unactivated Aryl Chlorides," *J. Am. Chem. Soc.*, 120(37): 9722–9723 (1998).

Onaivi, E.S., et al., "Chronic Nicotine Reverses Age–Associated Increases in Tail–Flick Latency and Anxiety in Rats," *Life Sciences*, 54(3): 193–202 (1994).

Overberger, et al., "Absolute Configuration of 2,7 Diazaspiro[4,4]nonane. A Reassignment," *J. Org. Chem.*, 46(13): 2757–2764 (1981).

Overman, L.E., and R.M. Burk, "A Convenient Synthesis of Unsymmetrical Secondary Amines. In Situ Formation of Unstable Formaldehyde Imines," *Tet. Lett.*, 25(16): 1635–1638 (1984).

Pedersen, M.L., and D.B. Berkowitz, "Formal α–Vinylation of Amino Acids. Use of a New Benzeneselenolate Equivalent," *J. Org. Chem.*, 58(25): 6966–6975 (1993).

Pomerleau, O.F., et al., "The Effects of Cigarette Smoking on Pain and Anxiety," *Addictive Behaviors*, 9: 265–271 (1984).

Pullan, R.D., et al. "Transdermal Nicotine for Active Ulcerative Colitis," *New England J. Med.*, 330(12): 811–815 (1994).

Radziszewski, J.G., et al., "Twisted Si=N Bonds: Matrix Isolation of Bridgehead Silanimines," *J. Am. Chem. Soc.*, 115(18): 8401–8408 (1993).

Ranganathan, D., et al., "Nitroethylene: A Stable, Clean, and Reactive Agent for Organic Synthesis," *J. Org. Chem.*, 45(7): 1185–1189 (1980).

Rapier, C., et al., "Stereoselective Nicotine–Induced Release of Dopamine from Striatal Synaptosomes: Concentration Dependence and Repetitive Stimulation," *J. Neurochem.*, 50(4): 1123–1130 (1988).

Reiter, L.A., "Synthesis of 4(5)–Acyl–, 1–Substituted 5–Acyl–, and 1–Substituted 4–Acyl–1H–iimidazoles from 4–aminosioxazoles," *J. Org. Chem.*, 52(13): 2714–2726 (1987).

Ricciardi, F.J., and P.H. Doukas, "Facile Synthesis of Styrlquinuclidines," *Heterocycles*, 24(4): 971–977 (1986).

Rice, L.M., et al., "Spiranes. V(1) A Synthetic Route to Symmetrical and Unsymmetrical 3,9–Diazaspiro[5.5]undecanes," *J. Het. Chem.*, 1(3): 125–127 (1964).

Rowell, P.P. and D.L. Winkler, "Nicotinic Stimulation of [$^3$H] Acetylcholine Release from Mouse Cerebral Cortical Synaptosomes," *J. Neurochem.*, 43(6): 1593–1598 (1984).

Sanberg, P.R., et al., "Nicotine Potentiation of Haloperidol–Induced Catalepsy: Striatal Mechanisms," *Pharmacol. Biochem. & Behavior*, 46: 303–307 (1993).

Sandor, N.T., et al. "Effect of nicotine on dopaminergic – cholinergic interaction in the striatum," *Brain Res.*, 567: 313–316 (1991).

Selnick, H.G., et al., "Preparation and Trapping of 3–Lithium–O–Lithiophenoxide," *Tet. Lett.*, 34(13): 2043–2046 (1993).

Smith, P.W., et al., "New Spiropiperidines as Potent and Selective Non–Peptide Tachykinin $NK_2$ Receptor Antagonists," *J. Med. Chem.*, 38(19): 3772–3779 (1995).

Süess, R. and A.G. Sandoz, "Regiospezifische Reduktionen von 1,3,3–trisubstituierten Succinimiden mit Diboran," *Helv. Chim. Acta*, 60: 1650–1656 (1977).

Sury, E., and K. Hoffmann, "Über Alkylenimin–Derivate. Beitrag zur Kenntnis der Diaza–spiro–undecane," *Helv. Chim. Acta*, 36: 1815–1820 (1953).

Thomas, J. and D. Clough, "The Preparation and Measurement of the Surface Activity of a Series of 4–Alkyl–1, 1'–Spirobipiperidinium Bromides," *J. Pharm. Pharmacol.*, 15(3): 167–177 (1963).

Toth, E., et al., "Effect of Nicotine of Extracellular Levels of Neurotransmitters Assessed by Microdialysis in Various Brain Regions: Role of Glutamic Acid," *Neurochem. Res.*, 17(3): 265–270 (1992).

Tripathi, H.L., et al., "Nicotine–Induced Antinociception of Rats and Mice: Correlation with Nicotine Brain Levels," *J. Pharmacol. Exp. Ther.*, 221(1): 91–96 (1982).

Vizi, E.S., "Acetylcholine release from guinea–pig ileum by parasympathetic ganglion stimulants and gastrin–like polypeptides," *Br. J. Pharmac.*, 47: 765–777 (1973).

Wagaw, S. and S.L. Buchwald, "The Synthesis of Aminopyridines: A Method Employing Palladium–Catalyzed Carbon–Nitrogen Bond Formation," *J. Org. Chem.*, 61(21): 7240–7241 (1996).

Wagner, B., et al., "Does Smoking Reduce the Risk of Neuroleptic Parkinsonoids?," *Pharmacopsychiat.*, 21: 302–303 (1988).

Wittekind, R.R., and C. Weissman, "Synthesis of the 1,8–Diazaspiro [4.5] decane System," *J. Het. Chem.*, 9(1): 111–113 (1972).

Williams, M., et al., "Neuronal Nicotinic Acetylcholine Receptors," *Drug News Perspec.*, 7(4): 205–223 (1994).

Zhu, J., et al. "Asymmetric Synthesis. 29.[1] Preparation of 1,8–Diazaspiro[5.5] undecane Derivatives," *J. Org. Chem.*, 58(23): 6451–6456 (1993).

Zwart, C., and J.P. Wibaut, "Chemical Behaviour of 3–Aminopyridine and of 3,5–Diaminopyridine. Syntheses of (3–Pyridyl)–Pyrazolones." *Recueil Trav. Chim. Pays–Bas*, 74(8/9): 1062–1069 (1955).

Delphion Printout—Bibliographic Data for EP 0417 631 A2 (Document F3) shows Derwent English language abstract. Oct. 21, 2003.

* cited by examiner

N-ARYL DIAZASPIRACYCLIC COMPOUNDS AND METHODS OF PREPARATION AND USE THEREOF

CROSS REFERENCE TO RELATED APPLICATION

This document claims priority to and the benefit of the filing date of provisional application entitled "N-Aryl Diazaspiracyclic Compounds and Methods of Preparation and Use Thereof" assigned Ser. No. 60/394,337, and filed Jul. 5, 2002, now abandoned, which is hereby incorporated by reference.

FIELD OF THE INVENTION

The present invention relates to pharmaceutical compositions incorporating compounds capable of affecting nicotinic cholinergic receptors, for example, as modulators of specific nicotinic receptor subtypes. The present invention also relates to methods for treating a wide variety of conditions and disorders, particularly those associated with dysfunction of the central and autonomic nervous systems.

BACKGROUND OF THE INVENTION

Nicotine exhibits a variety of pharmacological effects (Pullan et al., *N. Engl. J. Med.* 330:811–815 (1994)), some of which are due to neurotransmitter release (See, for example, Sjak-shie et al., *Brain Res.* 624:295 (1993), where neuroprotective effects of nicotine are proposed). For example, acetylcholine, dopamine, norepinephrine, serotonin and glutamate are released by neurons upon administration of nicotine (Rowell et al., *J. Neurochem.* 43:1593 (1984); Rapier et al., *J. Neurochem.* 50:1123 (1988); Sandor et al., *Brain Res.* 567:313 (1991) and Vizi, *Br. J. Pharmacol.* 47:765 (1973), (Hall et al., *Biochem. Pharmacol.* 21:1829 (1972), (Hery et al., *Arch. Int. Pharmacodyn. Ther.* 296:91 (1977)), and Toth et al., *Neurochem Res.* 17:265 (1992)). Confirmatory reports and additional recent studies show that nicotine administration modulates glutamate, nitric oxide, GABA, takykinins, cytokines and peptides in the central nervous system (CNS) (reviewed in Brioni et al., *Adv. Pharmacol.* 37:153 (1997)). Nicotine also reportedly potentiates the pharmacological behavior of certain pharmaceutical compositions used to treat certain disorders. See, for example, Sanberg et al., *Pharmacol. Biochem. & Behavior* 46:303 (1993); Harsing et al., *J. Neurochem.* 59:48 (1993) and Hughes, *Proceedings from Intl. Symp. Nic.* S40 (1994). Various additional beneficial pharmacological effects of nicotine have been proposed. See, for example, Decina et al., *Biol. Psychiatry* 28:502 (1990); Wagner et al., *Pharmacopsychiatry* 21:301 (1988); Pomerleau et al., *Addictive Behaviors* 9:265 (1984); Onaivi et al., *Life Sci.* 54(3):193 (1994); Tripathi et al., *J. Pharmacol. Exp. Ther.* 221:91(1982) and Hamon, *Trends in Pharmacol. Res.* 15:36 (1994).

In addition to nicotine itself, a variety of nicotinic compounds are purportedly useful for treating a wide variety of conditions and disorders. See, for example, Williams et al., *Drug News Perspec.* 7(4):205 (1994); Arneric et al., *CNS Drug Rev.* 1(1):1 (1995); Arneric et al., *Exp. Opin. Invest. Drugs* 5(1):79 (1996); Bencherife al., *J. Pharmacol. Exp. Ther.* 279:1413 (1996); Lippiello et al., *J. Pharmacol. Exp. Ther.* 279:1422 (1996); Damaj et al., *Neuroscience* (1997) *J. Pharmacol. Exp. Ther.* 291:390 (1999); Chiari et al., *Anesthesiology* 91:1447 (1999); Lavand'homme and Eisenbach, *Anesthesiology* 91:1455 (1999); Holladay et al., *J. Med. ChemChem.* 40(28): 4169 (1997); Bannon et al., *Science* 279: 77 (1998); PCT WO 94/08992, PCT WO 96/31475, PCT WO 96/40682, and U.S. Pat. No. 5,583,140 to Bencherif et al., U.S. Pat. No. 5,597,919 to Dull et al., U.S. Pat. No. 5,604,231 to Smith et al. and U.S. Pat. No. 5,852,041 to Cosford et al.

Nicotine and various nicotinic compounds are reportedly useful for treating a wide variety of CNS disorders. See, for example, U.S. Pat. Nos. 5,1871,166 to Kikuchi et al., U.S. Pat. No. 5,672,601 to Cignarella, PCT WO 99/21834 and PCT WO 97/40049, UK Patent Application GB 2295387 and European Patent Application 297,858. CNS disorders are a type of neurological disorder. They can be drug induced; attributed to genetic predisposition, infection or trauma; or of unknown etiology. CNS disorders include neuropsychiatric disorders, neurological diseases and mental illnesses, and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a deficiency of choline, dopamine, norepinephrine and/or serotonin.

Relatively common CNS disorders include pre-senile dementia (early-onset Alzheimer's disease), senile dementia (dementia of the Alzheimer's type), micro-infarct dementia, AIDS-related dementia, Creutzfeld-Jakob disease, Pick's disease, Parkinsonism including Parkinson's disease, progressive supranuclear palsy, Huntington's chorea, tardive dyskinesia, hyperkinesia, mania, attention deficit disorder, anxiety, dyslexia, schizophrenia, depression, obsessive-compulsive disorders and Tourette's syndrome.

A limitation of some nicotinic compounds is that they are associated with various undesirable side effects, for example, by stimulating muscle and ganglionic receptors. It would be desirable to have compounds, compositions and methods for preventing and/or treating various conditions or disorders (e.g., CNS disorders), including alleviating the symptoms of these disorders, where the compounds exhibit nicotinic pharmacology with a beneficial effect (e.g., upon the functioning of the CNS), but without significant associated side effects. It would further be highly desirable to provide compounds, compositions and methods that effect CNS function without significantly effecting those receptor subtypes which have the potential to induce undesirable side effects (e.g., appreciable activity at cardiovascular and skeletal muscle sites). The present invention provides such compounds, compositions and methods.

SUMMARY OF THE INVENTION

Compounds, pharmaceutical compositions including the compounds, and methods of preparation and use thereof are disclosed. The compounds are N-aryl diazaspirocyclic compounds, bridged analogs of N-heteroaryl diazaspirocyclic compounds, or prodrugs or metabolites of these compounds. The aryl group can be a five- or six-membered heterocyclic ring (heteroaryl). Examples of the N-aryl diazaspiocyclic compounds include 7-(3-pyridyl)-1,7-diazaspiro[4.4]nonane and 1-(3-pyridyl)-1,7-diazaspiro[4.4] nonane. Examples of bridged analogs of N-heteroaryl diazaspirocyclic compounds include 1'-(3-pyridyl)-spiro[1-azabicyclo[2.2.1]heptane-2,3'-pyrrolidine].

The compounds and compositions can be used to treat and/or prevent a wide variety of conditions or disorders, particularly those disorders characterized by dysfunction of nicotinic cholinergic neurotransmission, including disorders involving neuromodulation of neurotransmitter release, such as dopamine release. CNS disorders, which are characterized by an alteration in normal neurotransmitter release, are another example of disorders that can be treated and/or prevented. The compounds and compositions can also be used to alleviate pain. The methods involve administering to a subject an effective amount of an N-aryl diazaspirocyclic compound, bridged analog of an N-heteroaryl diazaspirocyclic compound, or prodrug or metabolite thereof to alleviate the particular disorder.

The pharmaceutical compositions include an effective amount of the compounds described herein. When employed in effective amounts, the compounds can interact with relevant nicotinic receptor sites of a subject and act as a therapeutic agent to prevent and/or treat a wide variety of conditions and disorders, particularly those disorders characterized by an alteration in normal neurotransmitter release. The pharmaceutical compositions provide therapeutic benefit to individuals suffering from such disorders and exhibiting clinical manifestations of such disorders. When employed in effective amounts, the compounds have the potential to: (i) exhibit nicotinic pharmacology and affect relevant nicotinic receptors sites (e.g., bind to nicotinic acetylcholine receptors and modulate their function, and/or (ii) modulate neurotransmitter secretion and thus prevent and suppress the symptoms associated with those diseases. In addition, the compounds can: (i) alter the number of nicotinic cholinergic receptors of the brain of the patient, (ii) exhibit neuroprotective effects and (iii) when employed in effective amounts, not result in appreciable adverse side effects (e.g., side effects such as significant increases in blood pressure and heart rate, significant negative effects upon the gastro-intestinal tract, and significant effects upon skeletal muscle). The pharmaceutical compositions are believed to be safe and effective with regards to prevention and treatment of a wide variety of conditions and disorders.

The foregoing and other aspects of the present invention are explained in detail in the detailed description and examples set forth below.

DETAILED DESCRIPTION OF THE INVENTION

Compounds, pharmaceutical compositions including the compounds, and methods of preparation and use thereof are disclosed.

The following definitions will be useful in understanding the metes and bounds of the invention as described herein.

As used herein, "alkyl" refers to straight chain or branched alkyl radicals including $C_1$–$C_8$, preferably $C_1$–$C_5$, such as methyl, ethyl, or isopropyl; "substituted alkyl" refers to alkyl radicals further bearing one or more substituent groups such as hydroxy, alkoxy, aryloxy, mercapto, aryl, heterocyclo, halo, amino, carboxyl, carbamyl, cyano, and the like; "alkenyl" refers to straight chain or branched hydrocarbon radicals including $C_1$–$C_8$, preferably $C_1$–$C_5$ and having at least one carbon-carbon double bond; "substituted alkenyl" refers to alkenyl radicals further bearing one or more substituent groups as defined above; "cycloalkyl" refers to saturated or unsaturated, non-aromatic, cyclic ring-containing radicals containing three to eight carbon atoms, preferably three to six carbon atoms; "substituted cycloalkyl" refers to cycloalkyl radicals further bearing one or more substituent groups as defined above; "aryl" refers to aromatic radicals having six to ten carbon atoms; "substituted aryl" refers to aryl radicals further bearing one or more substituent groups as defined above; "alkylaryl" refers to alkyl-substituted aryl radicals; "substituted alkylaryl" refers to alkylaryl radicals further bearing one or more substituent groups as defined above; "arylalkyl" refers to aryl-substituted alkyl radicals; "substituted arylalkyl" refers to arylalkyl radicals further bearing one or more substituent groups as defined above; "heterocyclyl" refers to saturated or unsaturated cyclic radicals containing one or more heteroatoms (e.g., O, N, S) as part of the ring structure and having two to seven carbon atoms in the ring; "substituted heterocyclyl" refers to heterocyclyl radicals further bearing one or more substituent groups as defined above.

I. Compounds

The compounds are N-aryl diazaspirocyclic compounds, bridged analogs of N-heteroaryl diazaspirocyclic compounds, prodrugs or metabolites of these compounds, and pharmaceutically acceptable salts thereof.

The compounds can bind to, and modulate nicotinic acetylcholine receptors in the patient's brain in the cortex, hippocampus, thalamus, basal ganglia, and spinal cord. When so bound, the compounds express nicotinic pharmacology and, in particular, modulate the release of various neurotransmitters including dopamine, other catecholamines such as norepinephrine, such as serotonin, acetylcholine, GABA, glutamate, neuropeptides, nitric oxide, cytokines and other neurotransmitters and neuromediators.

Receptor binding constants provide a measure of the ability of the compound to bind to half of the relevant receptor sites of certain brain cells of the patient. See, for example, Cheng et al., *Biochem. Pharmacol.* 22:3099 (1973). The receptor binding constants of the compounds described herein generally exceed about 0.1 nM, often exceed about 1 nM, and frequently exceed about 10 nM, and are often less than about 100 $\mu$M, often less than about 10 $\mu$M and frequently less than about 5 $\mu$M. Preferred compounds generally have receptor binding constanta less than about 2.5 $\mu$M, sometimes are less than about 1 $\mu$M, and can be less than about 100 nM.

The compounds described herein can demonstrate a nicotinic function by effectively activating neurotransmitter secretion from nerve ending preparations (i.e., synaptosomes). As such, these compounds can activate relevant neurons to release or secrete acetylcholine, dopamine, and other neurotransmitters. Generally, typical compounds activate dopamine secretion in amounts of at least one third, typically at least about 10 times less, frequently at least about 100 times less, and sometimes at least about 1,000 times less than those required for activation of muscle-type nicotinic receptors. Certain compounds elicit dopamine secretion in an amount which is comparable to that elicited by an equal molar amount of (S)-(−)-nicotine.

Preferably, the compounds can cross the blood-brain barrier, and thus enter the central nervous system of the patient. Log P values provide a measure of the ability of a compound to pass across a diffusion barrier, such as a biological membrane, including the blood brain barrier. See, for example, Hansch et al., *J. Med. Chem.* 11: 1 (1968). Typical log P values for the compounds described herein are generally greater than about −0.5, often are greater than about 0, and frequently are greater than about 0.5, and are typically less than about 3, often are less than about 2, and frequently are less than about 1.

In one embodiment, the compounds have the structure represented by Formula 1 below:

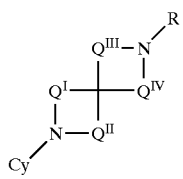

Formula 1

In the formula, $Q^I$ is $(CZ_2)_u$, $Q^{II}$ is $(CZ_2)_v$, $Q^{III}$ is $(CZ_2)_w$, and $Q^{IV}$ is $(CZ_2)_x$ where u, v, w and x are individually 0, 1, 2, 3 or 4, preferably 0, 1, 2 or 3. R is hydrogen, lower alkyl, acyl, alkoxycarbonyl or aryloxycarbonyl, preferably hydrogen or lower alkyl. When the value of u is 0, the value of v must be greater than 0, and, in the case of Formula 1, when the value of w is 0, the value of x must be greater than 0. In addition, the values of u, v, w and x are selected such that the diazaspirocyclic ring contains 7, 8, 9, 10 or 11 members, preferably 8, 9 or 10 members.

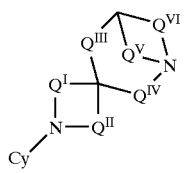

Formula 2

In another embodiment, the compounds are represented by Formula 2, above. In Formula 2 $Q^I$ is $(CZ_2)_u$, $Q^{II}$ is $(CZ_2)_v$, $Q^{III}$ is $(CZ_2)_w$, $Q^{IV}$ is $(CZ_2)_x$, $Q^V$ is $(CZ_2)_y$, and $Q^{VI}$ is $(CZ_2)_z$, where u, v, w, x, y and z are individually 0, 1, 2, 3 or 4, preferably 0, 1 or 2. The values of u, v, w, x, y and z are selected such that the bridged diazaspirocyclic ring contains 8, 9, 10, 11, 12 or 13 members, preferably 9, 10, 11 or 12 members. In the case of Formula 2, the values w and x can be simultaneously 0. In addition, R is hydrogen, lower alkyl, acyl, alkoxycarbonyl or aryloxycarbonyl, preferably hydrogen or lower alkyl.

Each individual Z represents either hydrogen or a suitable non-hydrogen substituent species (e.g., alkyl, substituted alkyl, cycloalkyl, substituted cycloalkyl, heterocyclyl, substituted heterocyclyl, aryl, substituted aryl, alkylaryl, substituted alkylaryl, arylalkyl or substituted arylalkyl; but preferably lower alkyl or aryl).

In either formula, Cy represents a suitable five- or six-membered heteroaromatic ring. In one embodiment, Cy is a six membered ring of the formula:

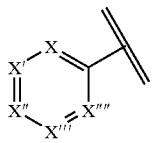

Each of X, X', X", X''' and X'''' is individually nitrogen, nitrogen bonded to oxygen (e.g., an N-oxide or N—O functionality) or carbon bonded to a substituent species. No more than three of X, X', X", X''' and X'''' are nitrogen or nitrogen bonded to oxygen, and it is preferred that only one or two of X, X', X", X''' and X'''' be nitrogen or nitrogen bonded to oxygen. In addition, it is highly preferred that not more than one of X, X', X", X''' and X'''' be nitrogen bonded to oxygen; and it is preferred that if one of those species is nitrogen bonded to oxygen, that species is X'''. Most preferably, X''' is nitrogen. In certain preferred circumstances, both X' and X''' are nitrogen. Typically, X, X" and X'''' are carbon bonded to a substituent species, and it is typical that the substituent species at X, X" and X'''' are hydrogen. For certain other preferred compounds where X''' is carbon bonded to a substituent species such as hydrogen, X and X" are both nitrogen. In certain other preferred compounds where X' is carbon bonded to a substituent species such as hydrogen, X and X''' are both nitrogen.

In another embodiment, Cy is a five 5-membered heteroaromatic ring, such as pyrrole, furan, thiophene, isoxazole, isothiazole, oxazole, thiazole, pyrazole, 1,2,4-oxadiazole, 1,3,4-oxadiazole and 1,2,4-triazole. Other examples of such rings are described in U.S. Pat. No. 6,022,868 to Olesen et al., the contents of which are incorporated herein by reference in their entirety. One way of depicting Cy is as follows:

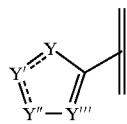

where Y and Y" are individually nitrogen, nitrogen bonded to a substituent species, oxygen, sulfur or carbon bonded to a substituent species, and Y' and Y''' are nitrogen or carbon bonded to a substituent species. The dashed lines indicate that the bonds (between Y and Y' and between Y' and Y") can be either single or double bonds. However, when the bond between Y and Y' is a single bond, the bond between Y' and Y" must be a double bond and vice versa. In cases in which Y or Y" is oxygen or sulfur, only one of Y and Y" is either oxygen or sulfur. At least one of Y, Y', Y" and Y''' must be oxygen, sulfur, nitrogen or nitrogen bonded to a substituent species. It is preferred that no more than three of Y, Y', Y" and Y''' be oxygen, sulfur, nitrogen or nitrogen bonded to a substituent species. It is further preferred that at least one, but no more than three, of Y, Y', Y" and Y''' be nitrogen.

Substituent species associated with any of X, X', X", X''', X'''', Y, Y', Y" and Y''' (when any is carbon bonded to a substituent species or nitrogen bonded to a substituent species), typically have a sigma m value between about −0.3 and about 0.75, frequently between about −0.25 and about 0.6; and each sigma m value individually can be 0 or not equal to zero; as determined in accordance with Hansch et al., *Chem. Rev.* 91:165 (1991).

Examples of suitable substituent species associated with any of X, X', X", X''', X'''', Y, Y', Y" and Y''' (when any is carbon bonded to a substituent species or nitrogen bonded to a substituent species), include hydrogen, alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, halo (e.g., F, Cl, Br, or I), —OR', —NR'R", —CF$_3$, —CN, —NO$_2$, —C$_2$R', —SR', —N$_3$, —C(=O)NR'R", —NR'C(=O)R", —C(=O)R', —C(=O)OR', —OC(=O)R', —O(CR'R")$_r$C(=O)R', —O(CR'R")$_r$NR"C(=O)R', —O(CR'R")$_r$NR" SO$_2$R', —OC(=O)NR'R", —NR'C(=O)O R", —SO$_2$R', —SO$_2$NR'R", and —NR'SO$_2$R", where R' and R" are individually hydrogen, lower alkyl (e.g., straight chain or branched alkyl including C$_1$–C$_8$, preferably C$_1$–C$_5$, such as methyl, ethyl, or isopropyl), cycloalkyl, heterocyclyl, aryl, or arylalkyl (such as benzyl), and r is an integer from 1 to 6. R' and R" can combine to form a cyclic functionality. The term "substituted" as applied to alkyl, aryl, cycloalkyl and the like refers to the substituents described above, starting with halo and ending with —NR'SO$_2$R".

Examples of suitable Cy groups include 3-pyridyl (unsubstituted or substituted in the 5 and/or 6 position(s) with any of the aforementioned substituents), 5-pyrimidinyl (unsubstituted or substituted in the 2 position with any of the aforementioned substituents), 4 and 5-isoxazolyl, 4 and 5-isothiazolyl, 5-oxazolyl, 5-thiazolyl, 5-(1,2,4-oxadiazolyl), 2-(1,3,4-oxadiazolyl) or 3-(1,2,4-triazolyl).

Representative aryl groups include phenyl, naphthyl, furanyl, thienyl, pyridinyl, pyrimidinyl, pyrazinyl, pyridazinyl, quinolinyl, and indolyl. Other representative aromatic ring systems are set forth in Gibson et al., *J. Med. Chem.* 39:4065 (1996). Any of these aromatic group containing species can be substituted with at least one substituent group, such as those described above that are associated with x' and the like. Representative substitevely include alkyl, aryl, halo, hydroxy, alkoxy, aryloxy or amino substituents.

Adjacent substituents of X, X', X", X'", X"", Y, Y', Y" and Y'" (when substituents are present) can combine to form one or more saturated or unsaturated, substituted or unsubstituted carbocyclic or heterocyclic rings containing, but not limited to, ether, acetal, ketal, amine, ketone, lactone, lactam, carbamate, or urea functionalities.

The compounds can occur in stereoisomeric forms, including both single enantiomers and racemic mixtures of such compounds, as well as mixtures of varying degrees of enantiomeric excess.

The compounds can be in a free base form or in a salt form (e.g., as pharmaceutically acceptable salts). Examples of suitable pharmaceutically acceptable salts include inorganic acid addition salts such as sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with an acidic amino acid such as aspartate and glutamate; alkali metal salts such as sodium and potassium; alkaline earth metal salts such as magnesium and calcium; ammonium salt; organic basic salts such as trimethylamine, triethylamine, pyridine, picoline, dicyclohexylamine, and N,N'-dibenzylethylenediamine; and salts with a basic amino acid such as lysine and arginine. The salts can be in some cases hydrates or ethanol solvates. The stoichiometry of the salt will vary with the nature of the components. Representative salts are provided as described in U.S. Pat. No. 5,597,919 to Dull et al., U.S. Pat. No. 5,616,716 to Dull et al. and U.S. Pat. No. 5,663,356 to Ruecroft et al., the disclosures of which are incorporated herein by reference in their entirety.

Representative compounds include the following:
7-(3-pyridyl)-1,7-diazaspiro[4.4]nonane
7-(5-pyrimidinyl)-1,7-diazaspiro[4.4]nonane
7-(5-isoxazolyl)-1,7-diazaspiro[4.4]nonane
7-(5-isothiazolyl)-1,7-diazaspiro[4.4]nonane
7-(5-(1,2,4-oxadiazol)yl)-1,7-diazaspiro[4.4]nonane
7-(2-(1,3,4-oxadiazol)yl)-1,7-diazaspiro[4.4]nonane
7-(2-pyrazinyl)-1,7-diazaspiro[4.4]nonane
7-(3-pyridazinyl)-1,7-diazaspiro[4.4]nonane
7-(5-methoxy-3-pyridyl)-1,7-diazaspiro[4.4]nonane
7-(5-cyclopentyloxy-3-pyridyl)-1,7-diazaspiro[4.4]nonane
7-(5-phenoxy-3-pyridyl)-1,7-diazaspiro[4.4]nonane
7-(5-(4-hydroxyphenoxy)-3-pyridyl)-1,7-diazaspiro[4.4]nonane
7-(5-ethynyl-3-pyridyl)-1,7-diazaspiro[4.4]nonane
7-(6-chloro-3-pyridyl)-1,7-diazaspiro[4.4]nonane
7-(6-methoxy-3-pyridazinyl)-1,7-diazaspiro[4.4]nonane
1-(3-pyridyl)-1,7-diazaspiro[4.4]nonane
1-(5-pyrimidinyl)-1,7-diazaspiro[4.4]nonane
1-(5-isoxazolyl)-1,7-diazaspiro[4.4]nonane
1-(5-isothiazolyl)-1,7-diazaspiro[4.4]nonane
1-(5-(1,2,4-oxadiazol)yl)-1,7-diazaspiro[4.4]nonane
1-(2-(1,3,4-oxadiazol)yl)-1,7-diazaspiro[4.4]nonane
1-(2-pyrazinyl)-1,7-diazaspiro[4.4]nonane
1-(3-pyridazinyl)-1,7-diazaspiro[4.4]nonane
1-methyl-7-(3-pyridyl)-1,7-diazaspiro[4.4]nonane
1-methyl-7-(5-pyrimidinyl)-1,7-diazaspiro[4.4]nonane
1-methyl-7-(5-isoxazolyl)-1,7-diazaspiro[4.4]nonane
1-methyl-7-(5-isothiazolyl)-1,7-diazaspiro[4.4]nonane
1-methyl-7-(5-(1,2,4-oxadiazol)yl)-1,7-diazaspiro[4.4]nonane
1-methyl-7-(2-(1,3,4-oxadiazol)yl)-1,7-diazaspiro[4.4]nonane
1-methyl-7-(2-pyrazinyl)-1,7-diazaspiro[4.4]nonane
1-methyl-7-(3-pyridazinyl)-1,7-diazaspiro[4.4]nonane
1-methyl-7-(5-methoxy-3-pyridyl)-1,7-diazaspiro[4.4]nonane
1-methyl-7-(5-cyclopentyloxy-3-pyridyl)-1,7-diazaspiro[4.4]nonane
1-methyl-7-(5-phenoxy-3-pyridyl)-1,7-diazaspiro[4.4]nonane
1-methyl-7-(5-(4-hydroxyphenoxy)-3-pyridyl)-1,7-diazaspiro[4.4]nonane
1-methyl-7-(5-ethynyl-3-pyridyl)-1,7-diazaspiro[4.4]nonane
1-methyl-7-(6-chloro-3-pyridyl)-1,7-diazaspiro[4.4]nonane
1-methyl-7-(6-methoxy-3-pyridazinyl)-1,7-diazaspiro[4.4]nonane
7-methyl-1-(3-pyridyl)-1,7-diazaspiro[4.4]nonane
7-methyl-1-(5-pyrimidinyl)-1,7-diazaspiro[4.4]nonane
7-methyl-1-(5-isoxazolyl)-1,7-diazaspiro[4.4]nonane
7-methyl-1-(5-isothiazolyl)-1,7-diazaspiro[4.4]nonane
7-methyl-1-(5-(1,2,4-oxadiazol)yl)-1,7-diazaspiro[4.4]nonane
7-methyl-1-(2-(1,3,4-oxadiazol)yl)-1,7-diazaspiro[4.4]nonane
7-methyl-1-(2-pyrazinyl)-1,7-diazaspiro[4.4]nonane
7-methyl-1-(3-pyridazinyl)-1,7-diazaspiro[4.4]nonane
2-(3-pyridyl)-2,7-diazaspiro[4.4]nonane
2-(5-pyrimidinyl)-2,7-diazaspiro[4.4]nonane
2-(5-isoxazolyl)-2,7-diazaspiro[4.4]nonane
2-(5-isothiazolyl)-2,7-diazaspiro[4.4]nonane
2-(5-(1,2,4-oxadiazol)yl)-2,7-diazaspiro[4.4]nonane
2-(2-(1,3,4-oxadiazol)yl)-2,7-diazaspiro[4.4]nonane
2-(2-pyrazinyl)-2,7-diazaspiro[4.4]nonane
2-(3-pyridazinyl)-2,7-diazaspiro[4.4]nonane
2-(5-methoxy-3-pyridyl)-2,7-diazaspiro[4.4]nonane
2-(5-cyclopentyloxy-3-pyridyl)-2,7-diazaspiro[4.4]nonane
2-(5-phenoxy-3-pyridyl)-2,7-diazaspiro[4.4]nonane
2-(5-(4-hydroxyphenoxy)-3-pyridyl)-2,7-diazaspiro[4.4]nonane
2-(5-ethynyl-3-pyridyl)-2,7-diazaspiro[4.4]nonane
2-(6-chloro-3-pyridyl)-2,7-diazaspiro[4.4]nonane
2-(6-methoxy-3-pyridazinyl)-2,7-diazaspiro[4.4]nonane
2-methyl-7-(3-pyridyl)-2,7-diazaspiro[4.4]nonane
2-methyl-7-(5-methoxy-3-pyridyl)-2,7-diazaspiro[4.4]nonane
2-methyl-7-(5-phenoxy-3-pyridyl)-2,7-diazaspiro[4.4]nonane
6-(3-pyridyl)-1,6-diazaspiro[3.4]octane
1-methyl-6-(3-pyridyl)-1,6-diazaspiro[3.4]octane
2-(3-pyridyl)-2,5-diazaspiro[3.4]octane
5-methyl-2-(3-pyridyl)-2,5-diazaspiro[3.4]octane 6-(3-pyridyl)-1,6-diazaspiro[3.5]nonane
1-methyl-6-(3-pyridyl)-1,6-diazaspiro[3.5]nonane
2-(3-pyridyl)-2,5-diazaspiro[3.5]nonane
5-methyl-2-(3-pyridyl)-2,5-diazaspiro[3.5]nonane
2-(3-pyridyl)-2,6-diazaspiro[4.5]decane
6-methyl-2-(3-pyridyl)-2,6-diazaspiro[4.5]decane
7-(3-pyridyl)-1,7-diazaspiro[4.5]decane
1-methyl-7-(3-pyridyl)-1,7-diazaspiro[4.5]decane
8-(3-pyridyl)-1,8-diazaspiro[5.5]undecane
1-methyl-8-(3-pyridyl)-1,8-diazaspiro[5.5]undecane Other representative compounds of the present invention include the following:

1'-(3-pyridyl)-spiro[1-azabicyclo[2.2.1]heptane-2,3'-pyrolidine]
1'-(5-ethoxy-3-pyridyl)-spiro[1-azabicyclo[2.2.1]heptane-2,3'-pyrrolidine]
1'-(5-cyclopentyloxy-3-pyridyl)-spiro[1-azabicyclo[2.2.1]heptane-2,3'-pyrrolidine]
1'-(5-phenoxy-3-pyridyl)-spiro[1-azabicyclo[2.2.1]heptane-2,3'-pyrrolidine]
1'-(5-(4-hydroxyphenoxy)-3-pyridyl)-spiro[1-azabicyclo[2.2.1]heptane-2,3'-pyrrolidine]
1'-(5-pyrimidinyl)-spiro[1-azabicyclo[2.2.1]heptane-2,3'-pyrrolidine]
1'-(5-isoxazolyl)-spiro[1-azabicyclo[2.2.1]heptane-2,3'-pyrrolidine]
1'-(5-isothiazolyl)-spiro[1-azabicyclo[2.2.1]heptane-2,3'-pyrrolidine]
1'-(5-(1,2,4-oxadiazol)yl)-spiro[1-azabicyclo[2.2.1]heptane-2,3'-pyrrolidine]
1'-(2-(1,3,4-oxadiazol)yl)-spiro[1-azabicyclo[2.2.1]heptane-2,3'-pyrrolidine]
1'-(2-pyrazinyl)-spiro[1-azabicyclo[2.2.1]heptane-2,3'-pyrrolidine]
1'-(3-pyridazinyl)-spiro[1-azabicyclo[2.2.1]heptane-2,3'-pyrrolidine]
1'-(5-ethynyl-3-pyridyl)-spiro[1-azabicyclo[2.2.1]heptane-2,3'-pyrrolidine]
1'-(6-chloro-3-pyridyl)-spiro[1-azabicyclo[2.2.1]heptane-2,3'-pyrrolidine]
1'-(6-methoxy-3-pyridazinyl)-spiro[1-azabicyclo[2.2.1]heptane-2,3'-pyrrolidine]
1'-(3-pyridyl)-spiro[1-azabicyclo[2.2.2]octane-2,3'-pyrrolidine]
1'-(5-methoxy-3-pyridyl)-spiro[1-azabicyclo[2.2.2]octane-2,3'-pyrrolidine]
1'-(5-cyclopentyloxy-3-pyridyl)-spiro[1-azabicyclo[2.2.2]octane-2,3'-pyrrolidine]
1'-(5-phenoxy-3-pyridyl)-spiro[1-azabicyclo[2.2.2]octane-2,3'-pyrrolidine]
1'-(5-(4-hydroxyphenoxy)-3-pyridyl)-spiro[1-azabicyclo[2.2.2]octane-2,3'-pyrrolidine]
1'-(5-ethynyl-3-pyridyl)-spiro[1-azabicyclo[2.2.2]octane-2,3'-pyrrolidine]
1'-(6-chloro-3-pyridyl)-spiro[1-azabicyclo[2.2.2]octane-2,3'-pyrrolidine]
1'-(5-pyrimidinyl)-spiro[1-azabicyclo[2.2.2]octane-2,3'-pyrrolidine]
1'-(2-pyrazinyl)-spiro[1-azabicyclo[2.2.2]octane-2,3'-pyrrolidine]
1'-(3-pyridazinyl)-spiro[1-azabicyclo[2.2.2]octane-2,3'-pyrrolidine]
1'-(6-methoxy-3-pyridazinyl)-spiro[1-azabicyclo[2.2.2]octane-2,3'-pyrrolidine]
1'-(5-isoxazolyl)-spiro[1-azabicyclo[2.2.2]octane-2,3'-pyrrolidine]
1'-(5-isothiazolyl)-spiro[1-azabicyclo[2.2.2]octane-2,3'-pyrrolidine]
1'-(5-(1,2,4-oxadiazol)yl)-spiro[1-azabicyclo[2.2.2]octane-2,3'-pyrrolidine]
1'-(2-(1,3,4-oxadiazol)yl)-spiro[1-azabicyclo[2.2.2]octane-2,3'-pyrrolidine]
1'-(3-pyridyl)-2'H-spiro[1-azabicyclo[2.2.1]heptane-7,3'-pyrrolidine]
1'-(5-methoxy-3-pyridyl)-2'H-spiro[1-azabicyclo[2.2.1]heptane-7,3'-pyrrolidine]
1'-(5-cyclopentyloxy-3-pyridyl)-2'H-spiro[1-azabicyclo[2.2.1]heptane-7,3'-pyrrolidine]
1'-(5-phenoxy-3-pyridyl)-2'H-spiro[1-azabicyclo[2.2.1]heptane-7,3'-pyrrolidine]
1'-(5-(4-hydroxyphenoxy)-3-pyridyl)-2'-spiro[1-azabicyclo[2.2.1]heptane-7,3'-pyrrolidine]
1'-(6-chloro-3-pyridyl)-2'H-spiro[1-azabicyclo[2.2.1]heptane-7,3'-pyrrolidine]
1'-(5-pyrimidinyl)-2'H-spiro[1-azabicyclo[2.2.1]heptane-7,3'-pyrrolidine]
1'-(2-pyrazinyl)-2'H-spiro[1-azabicyclo[2.2.1]heptane-7,3'-pyrrolidine]
1'-(3-pyridazinyl)-2'H-spiro[1-azabicyclo[2.2.1]heptane-7,3'-pyrrolidine]
1'-(6-methoxy-3-pyridazinyl)-2'H-spiro[1-azabicyclo[2.2.1]heptane-7,3'-pyrrolidine]
1'-(5-isoxazolyl)-2'H-spiro[1-azabicyclo[2.2.1]heptane-7,3'-pyrrolidine]
1'-(5-isothiazolyl)-2'H-spiro[1-azabicyclo[2.2.1]heptane-7,3'-pyrrolidine]
1'-(5-(1,2,4-oxadiazol)yl)-2'H-spiro[1-azabicyclo[2.2.1]heptane-7, II. Methods of Preparing the Compounds Scheme 1

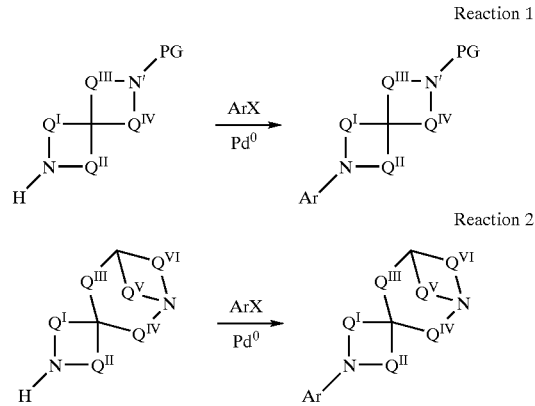

The compounds of Formulas 1 and 2 can be prepared using a general method involving arylation of one amino group of an optionally protected diazaspiroalkane (Scheme 1). Arylation at N with an appropriate aryl, or preferably heteroaryl, halide or triflate can be performed according to methods known to those skilled in the art, for example, employing metal (e.g., copper or palladium compounds) catalysis. The preferred general method in the present invention utilizes the teachings of Buchwald or Hartwig (Buchwald et al, *J. Org. Chem.*, 61: 7240 (1996); Hartwig et al., *J. Org. Chem.*, 64: 5575 (1999); see also Old et al., *J. Am. Chem. Soc.* 120: 9722 (1998)), wherein an amine is treated with a palladium(0) catalyst, a phosphine ligand and base. Thus, 1-benzyl-1,7-diazaspiro[4.4]nonane is reacted with 3-bromopyridine in the presence of tris(dibenzylideneacetone)dipalladium(0), 2,2'-bis(diphenylphosphino)-1,1'-binaphthyl and sodium tert-butoxide in toluene, to give 1-benzyl-7-(3-pyridyl)

diazaspiro[4.4]nonane. Removal of the benzyl group by hydrogenation, over 10% palladium on carbon, provides 7-(3-pyridyl)-diazaspiro[4.4]nonane. Alternatively, one skilled in the art will recognize that various protecting group strategies can be employed to provide products bearing an aryl group on nitrogen N', as opposed to N (Reaction 1, Scheme 1). A particularly useful combination of protecting groups in the present invention is benzyl and a carbamate, specifically, tert-butylcarbamate. Thus, 1-benzyl-1,7-diazaspiro[4.4]nonane is converted into 1-benzyl-7-(tert-butoxycarbonyl)-1,7-diazaspiro[4.4]nonane by treatment with di-tert-butyl dicarbonate. Subsequent hydrogenation and palladium-catalyzed arylation, with 3-bromopyridine, gives 7-(tert-butoxycarbonyl)-1-(3-pyridyl)diazaspiro[4.4]nonane. Removal of the tert-butoxycarbonyl group, with hydrochloric acid, provides 1-(3-pyridyl)-diazaspiro[4.4]nonane. Finally, in many cases where N and N' are sterically dissimilar, and whenever N is tertiary (as in Reaction 2, Scheme 1), selective arylation of N can be accomplished without first protecting N'. Thus, reaction of 1,7-diazaspiro[4.4]nonane with 3-bromopyridine, under the palladium-catalyzed conditions reported previously, gives almost exclusively 7-(3-pyridyl)-diazaspiro[4.4]nonane.

It will be obvious to those skilled in the art that incorporation of substituents on the heteroaryl ring introduced onto the diazaspiroalkane can be readily realized. Such substituents can provide useful properties in and of themselves or serve as a handle for further synthetic elaboration. A suitably protected heteroaryl diazaspiroalkane can be elaborated to give a number of useful compounds possessing substituents on the heteroaryl ring. For example, 1-benzyl-7-(5-bromo-3-pyridyl)-1,7-diazaspiro[4.4]nonane can be made by reacting 3,5-dibromopyridine with 1-benzyl-1,7-diazaspiro[4.4]nonane according to procedures described previously. The conversion of 1-benzyl-7-(5-bromo-3-pyridyl)diazaspiro[4.4]nonane into the corresponding 5-amino-substituted compound can be accomplished by the general method of Zwart et al., Recueil Trav. Chim. Pays-Bas 74: 1062 (1955), in which the bromo compound heated with aqueous ammonia in the presence of a copper catalyst. 5-Alkylamino substituted compounds can be prepared in a similar manner. 5-Ethynyl-substituted compounds can be prepared from the 5-bromo compound by palladium catalyzed coupling using 2-methyl-3-butyn-2-ol, followed by base-catalyzed (sodium hydride) removal of the acetone unit, according to the general techniques described in Cosford et al., J. Med. Chem. 39: 3235 (1996). The 5-ethynyl analogs can be converted into the corresponding 5-ethenyl, and subsequently to the corresponding 5-ethyl analogs by successive catalytic hydrogenation reactions. The 5-azido-substituted analogs can be prepared from the 5-bromo compound by reaction with lithium azide in N,N-dimethylformamide. 5-Alkylthio-substituted compounds can be prepared from the 5-bromo compound by reaction with an appropriate sodium alkylmercaptide (sodium alkanethiolate), using techniques known to those skilled in the art of organic synthesis.

A number of other analogs, bearing substituents in the 5 position of the pyridine ring, can be synthesized from the corresponding amino compounds, vide supra, via a 5-diazonium salt intermediate. Examples of other 5-substituted analogs that can be produced from 5-diazonium salt intermediates include, but are not limited to: 5-hydroxy, 5-alkoxy, 5-fluoro, 5-chloro, 5-iodo, 5-cyano, and 5-mercapto. These compounds can be synthesized using the general techniques set forth in Zwart et al., supra. For example, 1-benzyl-7-(5-hydroxy-3-pyridyl)-1,7-diazaspiro[4.4]nonane can be prepared from the reaction of the corresponding 5-diazonium salt intermediate with water. Likewise, 1-benzyl-7-(5-alkoxy-3-pyridyl)-1,7-diazaspiro[4.4]nonanes can be made from the reaction of the diazonium salt with alcohols. Appropriate 5-diazonium salts can be used to synthesize cyano or halo compounds, as will be known to those skilled in the art. 5-Mercapto substitutions can be obtained using techniques described in Hoffman et al., J. Med. Chem. 36: 953 (1993). The 5-mercaptan so generated can, in turn, be converted to a 5-alkylthio substitutuent by reaction with sodium hydride and an appropriate alkyl bromide. Subsequent oxidation would then provide a sulfone. 5-Acylamido analogs of the aforementioned compounds can be prepared by reaction of the corresponding 5-amino compounds with an appropriate acid anhydride or acid chloride using techniques known to those skilled in the art of organic synthesis.

5-Hydroxy-substituted analogs of the aforementioned compounds can be used to prepare corresponding 5-alkanoyloxy-substituted compounds by reaction with the appropriate acid, acid chloride, or acid anhydride. Likewise, the 5-hydroxy compounds are precursors of both the 5-aryloxy and 5-heteroaryloxy via nucleophilic aromatic substitution at electron deficient aromatic rings (e.g., 4-fluorobenzonitrile and 2,4-dichloropyrimidine). Such chemistry is well known to those skilled in the art of organic synthesis. Ether derivatives can also be prepared from the 5-hydroxy compounds by alkylation with alkyl halides and a suitable base or via Mitsunobu chemistry, in which a trialkyl- or triarylphosphine and diethyl azodicarboxylate are typically used. See Hughes, Org. React. (N.Y.) 42: 335 (1992) and Hughes, Org. Prep. Proced. Int. 28: 127 (1996) for typical Mitsunobu conditions.

5-Cyano-substituted analogs of the aforementioned compounds can be hydrolyzed to afford the corresponding 5-carboxamido-substituted compounds. Further hydrolysis results in formation of the corresponding 5-carboxylic acid-substituted analogs. Reduction of the 5-cyano-substituted analogs with lithium aluminum hydride yields the corresponding 5-aminomethyl analogs. 5-Acyl-substituted analogs can be prepared from corresponding 5-carboxylic acid-substituted analogs by reaction with an appropriate alkyllithium using techniques known to those skilled in the art of organic synthesis.

5-Carboxylic acid-substituted analogs of the aforementioned compounds can be converted to the corresponding esters by reaction with an appropriate alcohol and acid catalyst. Compounds with an ester group at the 5-pyridyl position can be reduced with sodium borohydride or lithium aluminum hydride to produce the corresponding 5-hydroxymethyl-substituted analogs. These analogs in turn can be converted to compounds bearing an ether moiety at the 5-pyridyl position by reaction with sodium hydride and an appropriate alkyl halide, using conventional techniques. Alternatively, the 5-hydroxymethyl-substituted analogs can be reacted with tosyl chloride to provide the corresponding 5-tosyloxymethyl analogs. The 5-carboxylic acid-substituted analogs can also be converted to the corresponding 5-alkylaminoacyl analogs by sequential treatment with thionyl chloride and an appropriate alkylamine. Certain of these amides are known to readily undergo nucleophilic acyl substitution to produce ketones. Thus, the so-called Weinreb amides (N-methoxy-N-methylamides) react with aryllithium reagents to produce the corresponding diaryl ketones. For example, see Selnick et al., Tet. Lett. 34: 2043 (1993).

5-Tosyloxymethyl-substituted analogs of the aforementioned compounds can be converted to the corresponding 5-methyl-substituted compounds by reduction with lithium aluminum hydride. 5-Tosyloxymethyl-substituted analogs of the aforementioned compounds can also be used to produce 5-alkyl-substituted compounds via reaction with an alkyllithium reagent. 5-Hydroxy-substituted analogs of the aforementioned compounds can be used to prepare 5-N-alkyl- or 5-N-arylcarbamoyloxy-substituted compounds by reaction with N-alkyl- or N-arylisocyanates. 5-Amino-substituted analogs of the aforementioned compounds can be used to prepare 5-alkoxycarboxamido-substituted compounds and 5-urea derivatives by reaction with alkyl chloroformate esters and N-alkyl- or N-arylisocyanates, respectively, using techniques known to those skilled in the art of organic synthesis.

Chemistries analogous to those described hereinbefore for the preparation of 5-substituted pyridine analogs of diazaspiro compounds can be devised for the synthesis of analogs bearing substituents in the 2, 4, and 6 positions of the pyridine ring. For example, a number of 2-, 4-, and 6-aminopyridyldiazaspiroalkanes can be converted to the corresponding diazonium salt intermediates, which can be transformed to a variety of compounds with substituents at the 2, 4, and 6 positions of the pyridine ring as was described for the 5-substituted analogs above. The requisite 2-, 4-, and 6-aminopyridyl diazaspiroalkanes are available via the Chichibabin reaction of unsubstituted pyridyl diazaspiroalkanes (e.g., 1-benzyl-7-(3-pyridyl)-1,7-diazaspiro[4.4]nonane, described previously) with sodium amide. Similar reactions are described in *Chemistry of Heterocyclic Compounds*, Volume 14, part 3, pp. 3–5 (Interscience Publishers, 1962) and by Lahti et al., *J. Med. Chem.* 42: 2227 (1999).

After the desired heteroaryl ring functional group manipulation has been accomplished, the optional protecting group can be removed from the diazabicycle using appropriate conditions. Thus, for example, hydrogenolysis of 1-benzyl-7-(5-alkoxy-3-pyridyl)-1,7-diazaspiro[4.4]nonane will generate 7-(5-alkoxy-3-pyridyl)-1,7-diazaspiro[4.4]nonane. Those skilled in the art of organic chemistry will appreciate the necessity of pairing protecting groups with the chemistries required to generate particular functionalities. In some cases it can be necessary, to retain a particular functionality, to replace one protecting group with another.

In an alternative approach to the synthesis of pyridine-substituted pyridyl diazaspiroalkanes, 3,5-dibromopyridine can be converted into the corresponding 5-alkoxy-3-bromo- and 5-aryloxy-3-bromopyridines by the action of sodium alkoxides or sodium aryloxides. Procedures such as those described by Comins et al., *J. Org. Chem.* 55: 69 (1990) and Hertog et al., *Recueil Trav. Chim. Pays-Bas* 74: 1171 (1955) are used. This is exemplified by the preparation 7-(5-(4-methoxyphenoxy)-3-pyridyl)-1,7-diazaspiro[4.4]nonane. Reaction of 3,5-dibromopyridine with sodium 4-methoxyphenoxide in N,N-dimethylformamide gives 3-bromo-5-(4-methoxyphenoxy)pyridine. Coupling of 3-bromo-5-(4-methoxyphenoxy)pyridine with 1-benzyl-7-(3-pyridyl)-1,7-diazaspiro[4.4]nonane in the presence of sodium tert-butoxide, and a catalytic amount of tris(dibenzylideneacetone)dipalladium(0) and 2,2'-bis(diphenylphosphino)-1,1'-binaphthyl, in toluene, followed by hydrogenolysis of the benzyl protecting group, will provide 7-(5-(4-methoxyphenoxy)-3-pyridyl)-1,7-diazaspiro[4.4]nonane.

Other aryl halides undergo the palladium-catalyzed coupling reaction described previously. Thus 7-(5-pyrimidinyl)-1,7-diazaspiro[4.4]nonane is prepared in a similar manner from 5-bromopyrimidine and optionally 1-position protected 1,7-diazaspiro[4.4]nonane followed by deprotection, if necessary. This technology is especially applicable in cases, such as 3-bromopyridine, 3,5-dibromopyridine, and 5-bromopyrimidine, where the aromatic ring is not activated toward nucleophilic aromatic substitution.

In some cases, coupling of the heteroaromatic ring to the diazaspirocycle can be accomplished without the use of palladium catalysis. Examples of both five- and six-membered heteroaromatic ring compounds, which are activated toward nucleophilic aromatic substitution, are known by those skilled in the art of organic synthesis. For example, 7-(6-chloro-3-pyridazinyl)-1,7-diazaspiro[4.4]nonane can be synthesized from 3,6-dichloropyridazine and 1,7-diazaspiro[4.4]nonane. Likewise, 2,6-dicloropyrazine, and 2-bromothiazole will react with 1,7-diazaspiro[4.4]nonane to give 7-(6-chloro-2-pyrazinyl)-1,7-diazaspiro[4.4]nonane and 7-(2-thiazoyl)-1,7-diazaspiro[4.4]nonane, respectively.

The coupling reactions described in this application, whether palladium catalyzed or not, are amenable to high through-put synthetic techniques. Thus a library of compounds of the present invention can be produced by coupling, in a 96-well plate format, for instance, various haloarenes with various diazaspiro compounds.

Specific Diazaspiro Ring Systems

Optionally protected diazaspiroalkane intermediates used to prepare the compounds of Formulas I and II can be prepared by numerous methods. Several of these diazaspiroalkane intermediates are known and can be prepared using prior art methods. However, the synthesis of the intermediates using palladium chemistry is new to the art, and the pharmaceutical activity of the intermediates was not appreciated in the prior art.

The compounds of Formula 1, where u=v=1, w=0 and x=3, possess a 2,5-diazaspiro[3,4]octane core which can be prepared as depicted in Scheme 2.

Alkylation of N-benzyl-L-proline ethyl ester (Aldrich Chemical), using a strong base such as lithium diisopropylamide (LDA) and the aminomethyl equivalent cyanomethylbenzylamine, provides a beta-lactam, according to the procedure reported by Overman, *J. Am. Chem. Soc.* 107:1698 (1985) and *Tet. Lett.* 25: 1635 (1985). This can subsequently be reduced with lithium aluminum hydride to provide the 2,5-dibenzyl derivative of 2,5-diazaspiro[3,4]octane. Removal of the benzyl protecting groups, by either hydrogenation or oxidative cleavage with, for example, ceric ammonium nitrate, will produce 2,5-diazaspiro[3,4]octane. Alternatively, chemistry similar to that described in EP patent application 90117078.7 (publication number EP 0 417 631) can be used to produce a geminal bis(hydroxymethyl) derivative and subsequently convert it to the desired 2,5-diazaspiro[3,4]octane (Scheme 2). The subsequent palladium-catalyzed arylation, as described previously, would be expected to proceed with selectivity for the less sterically hindered azetidinyl nitrogen, producing 2-aryl-2,5-diazaspiro[3,4]octanes. The isomeric 5-aryl-2,5-diazaspiro[3,4]octanes can be made by first protecting the azetidinyl nitrogen (with, for instance, a carbamate) and then performing the arylation, followed by deprotection.

Scheme 2

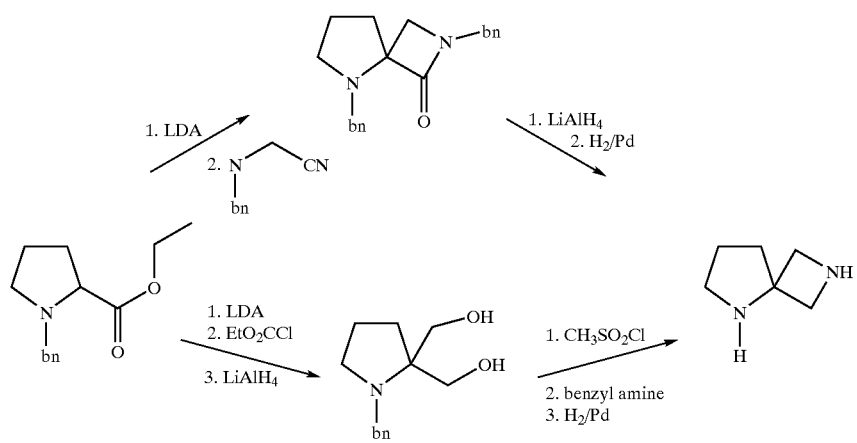

The compounds of Formula 1, wherein u=2, v=1, w=0 and x=3, possess the 1,7-diazaspiro[4.4]nonane system which can be prepared according to numerous methods, several of which are shown above in Scheme 3. In one embodiment (Method A), a suitably protected proline ester, for example N-benzyl-L-proline ethyl ester, can be deprotonated with lithium diisopropylamide and allowed to react by Michael addition to nitroethylene. This provides methyl 2-(2-nitroethyl)-1-benzylpyrrolidine-2-carboxylate. Subsequent reduction of the nitro group using Raney nickel, followed by lactamization by methods known to those skilled in the art (for example, heating in a suitable solvent with or without an acidic or basic catalyst), provides 1-benzyl-1,7-diazaspiro [4.4]nonan-6-one.

The 1,7-diazaspiro[4.4]nonane-6-one can alternatively be prepared according to one of several other methods reported in the literature. Such teachings indicate that a suitably protected proline ester can be deprotonated with lithium diisopropylamide and allowed to react with an alkylating agent such as chloroacetonitrile, then subjected to nitrile reduction and cyclization (Method B, Scheme 3) as reported by Culbertson et al., *J. Med. Chem.* 33:2270 (1990).

Other teachings indicate that a suitably protected proline ester can be deprotonated with lithium diisopropylamide and allowed to react with an alkylating agent such as allyl bromide (Method C, Scheme 3). The resulting olefin can then be oxidatively cleaved to an aldehyde, as reported by Genin et al., *J. Org. Chem.* 58:2334 (1993); Hinds et al., *J. Med. Chem.* 34:1777 (1991); Kim et al., *J. Org. Chem.* 61:3138 (1996); EP 0 360 390 and U.S. Pat. No. 5,733,912. The aldehyde can then be subjected to reductive amination with an ammonium salt or primary aliphatic or aromatic amine, according to methods known to those skilled in the art. Alternatively, the aldehyde can be reduced to the corresponding alcohol and the alcohol then transformed to an amine by conversion to a leaving group, followed by displacement with the appropriate amine. This can also be achieved by displacing the leaving group with an azide ion and subsequently reduction to the primary amine using methods known to those skilled in the art. The alcohol can be converted to an amine using Mitsunobu conditions, as discussed previously. The alkyl 2-aminoethyl pyrrolidine-2-carboxylate, obtained according to one of the methods described above, can be cyclized to a spirolactam by methods known to those skilled in the art, such as heating in a suitable solvent with or without an acidic or basic catalyst.

The lactam obtained by any one of the above methods (Methods A, B or C) can be treated with a suitable reducing agent, such as lithium aluminum hydride, to provide the protected 1,7-diazaspiro[4.4]nonane, in this example, 1-benzyl-1,7-diazaspiro[4.4]nonane. The protecting group can be removed using methods known those skilled in the art to provide the desired 1,7-diazaspiro[4.4]nonane. Arylation at either nitrogen can be accomplished using methods described herein.

Scheme 3

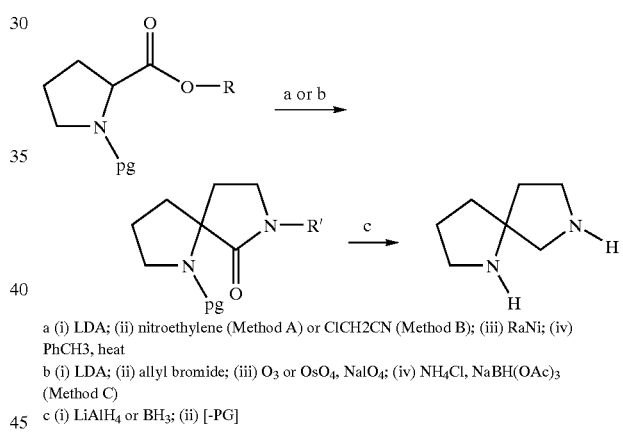

a (i) LDA; (ii) nitroethylene (Method A) or ClCH2CN (Method B); (iii) RaNi; (iv) PhCH3, heat b (i) LDA; (ii) allyl bromide; (iii) O3 or OsO4, NaIO4; (iv) NH4Cl, NaBH(OAc)3 (Method C)

c (i) LiAlH4 or BH3; (ii) [-PG]

Alternatively, the 1,7-diazaspiro[4.4]nonane core can also be prepared according to Scheme 4. The conversion of 1,4-dioxaspiro[4.5]decan-8-one to 4-benzoyloxycyclohexanone can be readily achieved by those skilled in the art. Subsequent transformation of 4-benzoyloxycyclohexanone to 1,7-diazaspiro[4.4]nonane (through the intermediacy of 4-oxocaprolactam, as shown) can be performed according to the teachings of Majer et al., *Coll. Czech. Chem. Comm.* 47:950 (1982).

Scheme 4

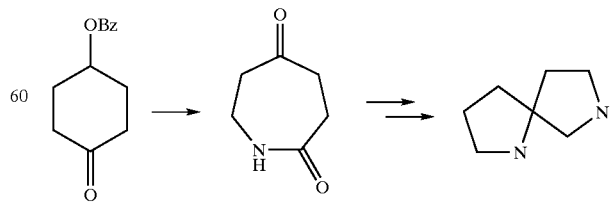

The compounds of Formula 1, wherein u=2, v=1, w=1 and x=2, possess the symmetrical 2,7-diazaspiro[4,4]nonane system which can be prepared according to Scheme 5. This method is reported by Overman et al., *J. Org. Chem.* 46: 2757 (1981) and Culbertson et al., *J. Med. Chem.* 33:2270 (1990).

Scheme 5

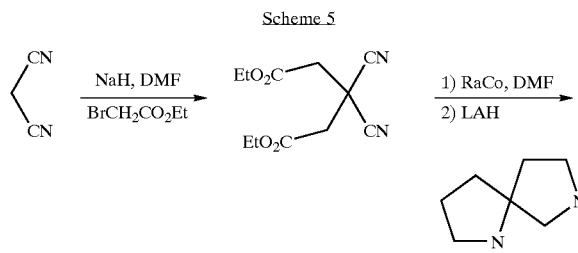

The compounds of Formula 1, wherein u=3, v=1, w=0 and x=3, possess the 1,7-diazaspiro[4.5]decane system which can be prepared according to Scheme 6. The teachings of Kim et al., *J. Org. Chem.* 61:3138 (1996), patent EP360390 and U.S. Pat. No. 5,733,912 indicate that a suitably protected proline ester (e.g., N-benzyl-L-proline ethyl ester) can be deprotonated with lithium diisopropylamide and allowed to react with an alkylating agent such as allyl bromide. U.S. Pat. No. 5,733,912 also teaches that hydroboration/oxidation of the allyl side chain can be performed to provide the 2-(3-hydroxypropyl) group. Those skilled in the art will appreciate that the hydroxyl group can then be converted to an amino group by a number of methods, for example oxidation followed by reductive amination. Alternatively, a suitably protected proline ester can be deprotonated with lithium diisopropylamide and allowed to react with an alkylating agent such as diiodopropane. Conversion of the primary iodide to an amine can then be performed according to known methods, for example treatment with ammonia in the presence of a copper catalyst. The resulting amino ester can be cyclized to afford a protected 1,7-diazaspiro[4.5] decan-6-one using any number of known procedures, for example heating in a suitable solvent in the presence or absence of an acidic or basic catalyst, as discussed previously. Alternatively, the known 1,7-diaza-spiro[4.5]decan-6-one can be prepared according to the teachings of Loefas et al., *J. Het. Chem.* 21:583 (1984), in which the ring contraction of 2,10-diazabicyclo[4.4.0]dec-1-ene is used.

The 1,7-diazaspiro[4.5]decan-6-one, obtained by any of the above methods, can then be treated with a reducing agent, such as lithium aluminum hydride, followed by removal of the protecting group, to provide the desired 1,7-diazaspiro[4.5]decane. Arylation can then be carried out at either nitrogen using methods described herein.

Scheme 6

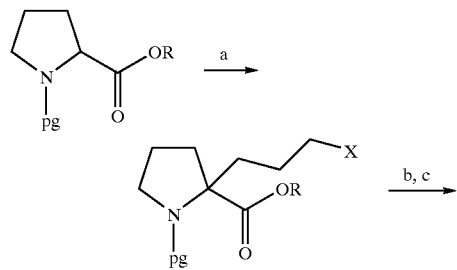

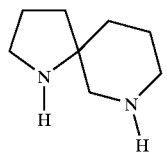

a X = OH: (i) LDA, allyl bromide; (ii) BH$_3$, H$_2$O$_2$  X = I: LDA, 1,3-diiodopropane
b X = OH: (i) PCC or Swern; (ii) NH$_4$Cl, NaBH(OAc)$_3$; (iii) heat (+catalyst?)
X = I: (i) NH$_3$, CuI; (ii) heat (+catalyst?)
c (i) BH$_3$ or LiAlH$_4$; (ii) [-PG]

The compounds of Formula 1, wherein u=2, v=1, w=0, and x=4, possess the 2,6-diazaspiro[4.5]decane core which can be prepared according to the method of Ciblat, et al., *Tet. Lett.* 42: 4815 (2001). Thus, commercially available 1-benzyl-3-pyrrolidinone can be reacted with 2-methyl-2-(2-aminoethyl)-1,3-dioxolane (Islam and Raphael, *J. Chem. Soc.* 3151 (1955)) in an intramolecular Mannich reaction. The product, the ethylene ketal of 2-benzyl-2,10-diazaspiro[4.5]decan-7-one, can then be hydrolyzed to the ketone, using aqueous hydrochloric acid. Deoxygenation of the ketone can then be accomplished by standard methods, such as conversion to the corresponding 1,3-dithiane, followed by treatment with Raney nickel. The 2-benzyl-2,6-diazaspiro[4.5]decane thus produced can be directly arylated on the 6-position nitrogen or converted into 6-(tert-butoxycarbonyl)-2,6-diazaspiro[4.5]decane by treatment with di-tert-butyl dicarbonate, followed by hydrogenation. The latter derivative can then be arylated at the 2-position nitrogen. Similar chemistry can be used to convert other azacyclic ketones into the corresponding spirodiaza compounds. Thus, reaction of any of various N-protected 3-azetidinones (the synthesis of which is described by Lall, et al., *J. Org. Chem.* 67: 1536 (2002) and Marchand, et al., *Heterocycles* 49: 149 (1998)) with 2-methyl-2-(2-aminoethyl)-1,3-dioxolane, followed by deoxygenation (as described above), will produce the corresponding protected 2,5-diazaspiro[3.5]nonane (Formula 1, wherein u=1, v=1, w=0, and x=4).

The compounds of Formula 1, wherein u=v=2, w=0, and x=3, possess the 1,8-diazaspiro[4.5]decane core which can be prepared according to Scheme 7. According to the teachings reported by Wittekind et al., *J. Het. Chem.* 9:11 (1972), a protected 4-piperidone can be converted to the 4-nitropiperidine. Subsequent Michael addition with ethyl acrylate, for example, followed by reduction of the nitro group with Raney nickel, provides the 1,8-diazaspiro[4.5]decan-2-one. This lactam can be reduced with an appropriate reducing agent, such as lithium aluminum hydride, followed by removal of the protecting group, to provide the optionally substituted 1,8-diazaspiro[4.5]decane. Arylation on either nitrogen can be accomplished using methods described herein.

Scheme 7

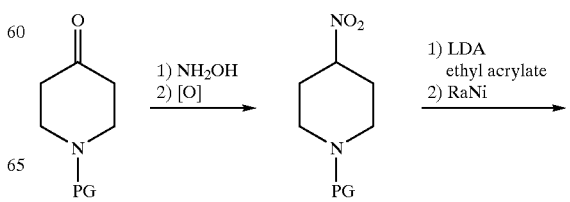

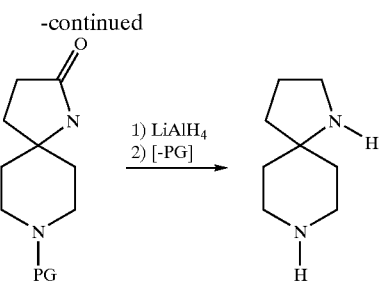

The compounds of Formula 1, wherein u=2, v=1, and w=x=2, possess the 2,8-diazaspiro[4.5]decane core which can be prepared according to Scheme 8. According to various teachings (*Helv. Chim. Acta* 60: 1650 (1977); Smith et al., *J. Med. Chem.* 19:3772 (1995); Elliott et al., *Biorg. Med. Chem. Lett.* 8:1851 (1998)), a protected 4-piperidone can be converted to the 4-piperidinylidene acetic acid ester via Wittig olefination. Subsequent Michael addition with the anion of nitromethane, followed by reduction of the nitro group and spontaneous cyclization with Raney nickel, provides the protected 2,8-diazaspiro[4.5]decan-3-one. Treatment of the protected 2,8-diazaspiro[4.5]decan-3-one with a reducing agent, such as lithium aluminum hydride, followed by removal of the protecting group, provides the 2,8-diazaspiro[4.5]decane. Arylation can be accomplished on either nitrogen using the methods described herein.

Scheme 8

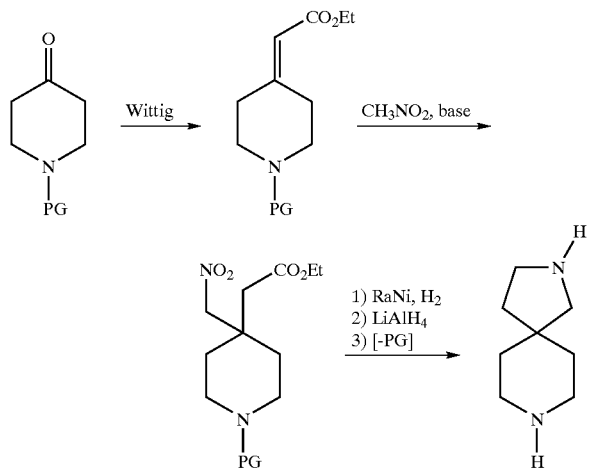

The compounds of Formula 1, wherein u=2, v=1, w=4 and x=0, possess the 1,8-diazaspiro[5.5]decane core and can be prepared according to the procedures utilized for the analogous 1,7-diazaspiro[4.4]nonanes by substituting pipecolinate ester for proline ester. Alternatively, the procedure reported in Zhu et al., *J. Org. Chem.* 58:6451 (1993) can be employed.

The compounds of Formula 1 wherein u=3, v=1, w=1 and x=3, possess the symmetrical 2,8-diazaspiro[5.5]undecane core and can be prepared according to the procedures reported in *Helv. Chim. Acta* 36:1815 (1953), *J. Org. Chem.* 28:336 (1963) or, preferably, Culbertson et al., *J. Med. Chem.* 33:2270 (1990).

The compounds of Formula 1 wherein u=v=2 and w=x=2, possess the symmetrical 3,9-diazaspiro[5.5]undecane core and can be prepared according to procedures reported in Rice et al., *J. Het. Chem.* 1: 125 (1964), U.S. Pat. No. 3,282,947, or *J. Med. Chem.* 8:62 (1965).

Single enantiomer compounds of the present invention can be made by various methods. One method, well known to those skilled in the art of organic synthesis, involves resolution using diastereomeric salts. Compounds of the present invention contain basic nitrogen atoms and will react with acids to form crystalline salts. Various acids, carboxylic and sulfonic, are commercially available in enantiomerically pure form. Examples include tartaric, dibenzoyl- and di-p-toluoyltartaric, and camphorsulfonic acids. When any one of these or other single enantiomer acids is reacted with a racemic amine base, diastereomeric salts result. Fractional crystallization of the salts, and subsequent regeneration of the bases, results in enantiomeric resolution thereof.

Another means of separation of involves conversion of the enantiomeric mixture into diastereomeric amides or carbamates, using a chiral acid or chloroformate. Thus, when racemic 7-(3-pyridyl)-1,7-diazaspiro[4.4]nonane is coupled with N-(tert-butoxycarbonyl)-S-proline, using diphenyl chlorophosphate, and the protecting group removed (with trifluoroacetic acid), the resulting diastereomeric proline amides of 7-(3-pyridyl)-1,7-diazaspiro[4.4] nonane are separable by liquid chromatography. The separated amides are then transformed into (+) and (−) 7-(3-pyridyl)-1,7-diazaspiro[4.4]nonane by the Edman degradation.

Selective synthesis of single enantiomers can also be accomplished by methods known to those skilled in the art. Such methods will vary as the chemistry used for construction of the diazaspiro rings varies. For instance, for the syntheses in which the alkylation of a proline derivative is used to form the diazaspiro system (such as described for the 1,7-diazaspiro[4.4]nonane system), the alkylation of proline can be carried out in a stereospecific manner. Thus, methods such as those described by Beck et al., *Org. Synth.* 72: 62 (1993) or Wang and Germanas, *Synlett:* 33 (1999) (and references therein) can be used to control the stereochemistry of the alkylation step. When enantiomerically pure proline ester (commercially available from Aldrich) is used as the starting material for such a process, the alkylation product is also a single enantiomer. A variety of electrophiles can be used in such alkylations, including allyl halides, which have been useful in assembling spiro systems related to compounds of the present invention Genin and Johnson, *J. Amer. Chem. Soc.* 114: 8778 (1992).

Bridged Spiro Ring Systems

The compounds of Formula 2, wherein u=1, v=2, w=0, x=0, y=2 and z=2, possess the spiro[1-azabicyclo[2.2.1] heptane-7,3'-pyrrolidine] core and can be prepared according to Scheme 9. The anion of ethyl nitroacetate, formed in the presence of an amine base, can be condensed with tetrahydropyran-4-one using the procedure reported in Fomicola et al., *J. Org. Chem.* 63:3528 (1998). Simultaneous reduction of the nitro group and the olefin under catalytic hydrogenation conditions provides the 2-(4-oxanyl)glycine ester. This compound can be treated with hydrobromic acid to afford a dibromide, which is cyclized under basic conditions to the azabicyclo[2.2.1]heptane-7-carboxylic acid. Treatment of the acid with ethanol and sulfuric acid provides the ethyl azabicyclo[2.2.1]heptane-7-carboxylate. This compound is then deprotonated with lithium diisopropylamide and reacted by Michael addition with nitroethylene to give the ethyl aza-7-(2-nitroethyl) bicyclo[2.2.1]heptane-7-carboxylate. Reduction of the nitro group with Raney nickel, followed by spontaneous cyclization, affords the spirolactam. Treatment of the lactam with lithium aluminum hydride affords the spiro[1-azabicyclo[2.2.1]heptane-7,3'-pyrrolidine], which is subsequently arylated on the pyrrolidine nitrogen to produce compounds of the present invention.

Scheme 9

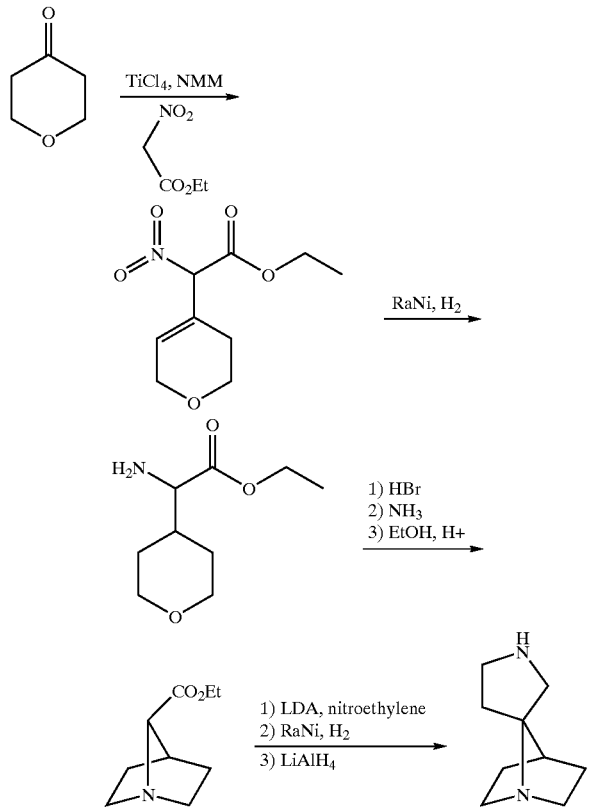

The compounds of Formula 2, wherein u=1, v=2, w=1, x=0, y=1 and z=2, possess the spiro[1-azabicyclo[2.2.1] heptane-2,3'-pyrrolidine] ring system and can be prepared according to Scheme 10. Conversion of tetrahydrofuran-3-ylmethanol (Aldrich) to 3-(bromomethyl)tetrahydrofuran can be achieved through mesylation and subsequent treatment with lithium bromide. The reaction of ethyl glycinate with benzophenone imine provides ethyl 3-aza-4,4-diphenyl-but-3-enoate which serves to both protect the amine and activate the methylene carbon toward alkylation. Alkylation of this imine can be performed, according to the method of Hansen, *J. Org. Chem.* 63:775 (1998), by deprotonating with potassium tert-butoxide and reacting with the 3-(bromomethyl)tetrahydrofuran. Deprotection under acidic conditions gives the desired 2-amino-3-(tetrahydrofuran-3-yl) propionic ester. Ring opening of the tetrahydrofuran can be achieved by treatment with hydrobromic acid to afford the dibromoamino acid intermediate, which, upon heating under basic conditions, cyclizes to the 1-azabicyclo[2.2.1] heptane-2-carboxylic acid. This acid iscan subsequently converted to the ethyl ester, using ethanol and sulfuric acid. Alkylation iscan then performed by deprotonation with lithium diisopropylamide and reaction with nitroethylene. Subsequent reduction of the nitro group using Raney nickel, followed by lactamization by methods known to those skilled in the art, gives the spiro[1-azabicyclo[2.2.1] heptane-2,3'-pyrrolidine]-2'-one. Treatment of the lactam with lithium aluminum hydride, gives the desired spiro[1-azabicyclo[2.2.1]heptane-2,3'-pyrrolidine], which is subsequently arylated on the pyrrolidine nitrogen to give compounds of the present invention.

Scheme 10

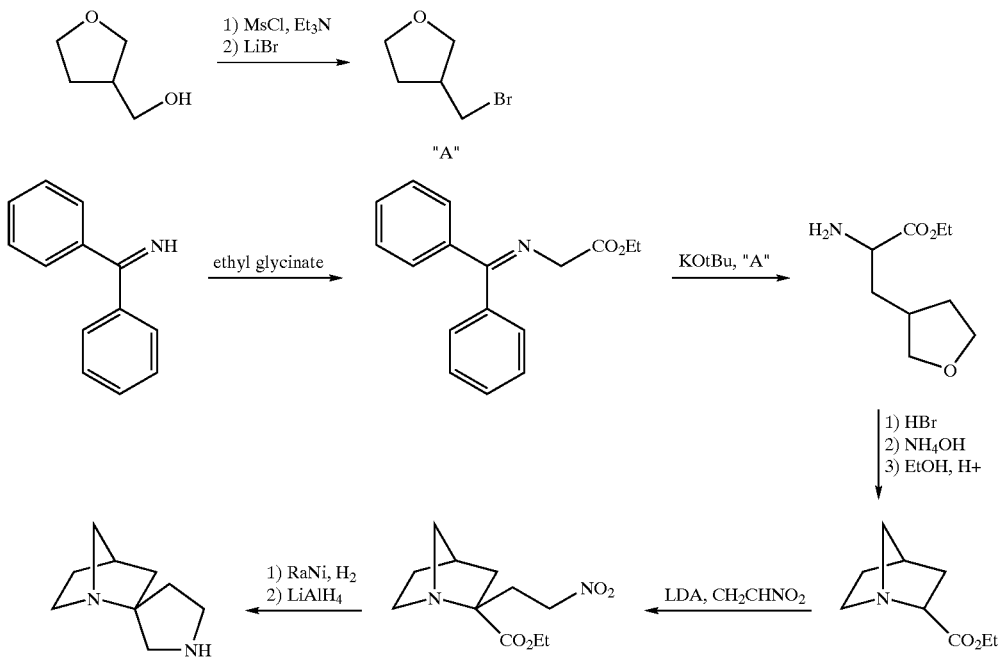

The compounds of Formula 2, wherein u=1, v=2, w=1, x=0, y=2 and z=2, possess the spiro[1-azabicyclo[2.2.2]octane-2,3'-pyrrolidine] core and can be prepared in a manner similar to that for the corresponding spiro[1-azabicyclo[2.2.1]heptane-2,3'-pyrrolidine], as seen in Scheme 11. Ethyl quinuclidine-2-carboxylate can be generated from (4-bromomethyl)tetrahydropyran by the procedures discussed previously for ethyl 1-azabicyclo[2.2.1]heptane-2-carboxylate. The requisite 4-(bromomethyl)tetrahydropyran can be prepared according to procedures found in Burger, et al., *J. Am. Chem. Soc.* 72:5512 (1950), Thomas, et al., *J. Pharm. Pharmacol.* 15:167 (1963) and *J. Am. Chem. Soc.* 115:8401 (1993). Ethyl quinuclidine-2-carboxylate iscan then deprotonated with lithium diisopropylamide and reacted with nitroethylene. Subsequent treatment with Raney nickel gives directly the spirolactam, spiro[azabicyclo[2.2.2]octane-2,3'-pyrrolidine]-2'-one, by reduction of the nitro group followed by spontaneous cyclization. This lactam iscan then reduced with lithium aluminum hydride to provide the desired spiro[1-azabicyclo[2.2.2]octane-2,3'-pyrrolidine], which is then arylated on the pyrrolidine nitrogen.

Scheme 12

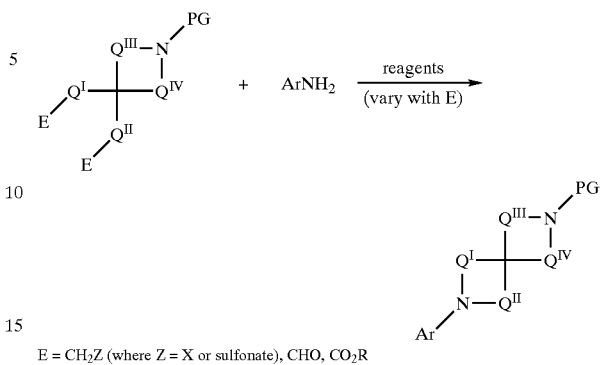

$E = CH_2Z$ (where $Z = X$ or sulfonate), CHO, $CO_2R$

The requisite bis-electrophiles can be synthesized by many diverse methods. Schemes 2, 3 and 6 all incorporate such intermediates (in reaction with benzylamine or ammonia). Pedersen, et al., *J. Org. Chem.* 58: 6966 (1993) and Scheme 11

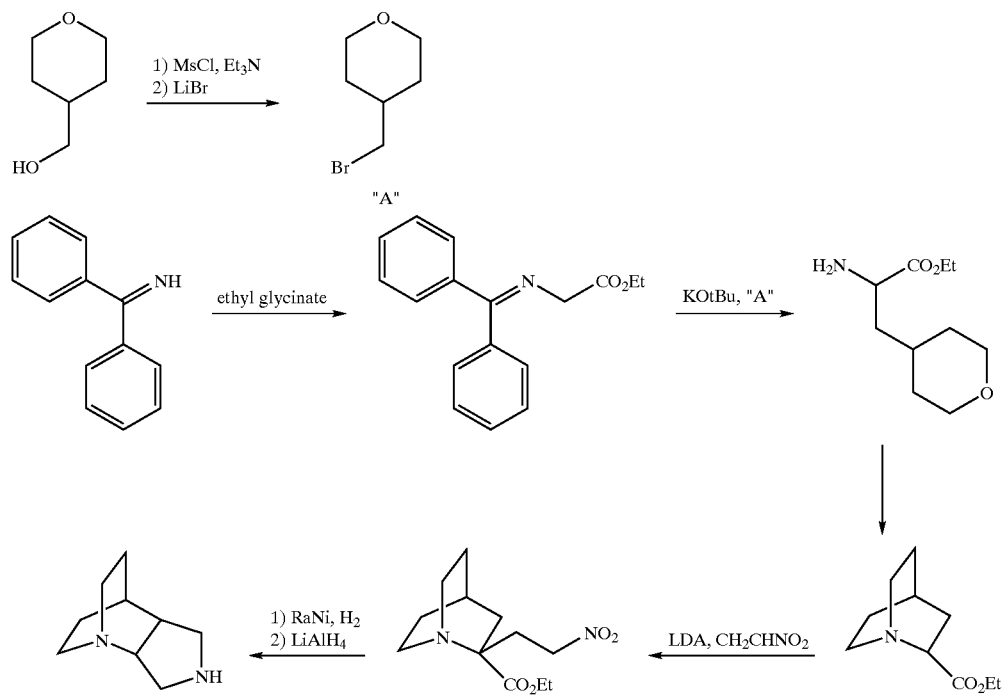

Alternate Synthetic Methods

The compounds can be produced using varying methods. Alternatives to the palladium catalyzed coupling protocol described above can be used. For instance, those skilled in the art of organic synthesis will recognize that one or more of the nitrogen containing rings can be formed by any one of many common amine syntheses. Thus, an arylamine can be reacted with a protected cyclic amine derivative (see scheme 12), which contains two reactive electrophiles, to generate an N-aryldiazaspiro compound. A variety of electrophiles participate in such chemistry (e.g., halides and sulfonates via nucleophilic displacement, aldehydes via reductive amination, esters and other acid derivatives via acyl substitution, followed by reduction).

Berkowitz, et al., *J. Org. Chem.* 60: 1233 (1995) both report the alkylation of dianions of N-acyl α-aminoesters. These alkylations also can be used for synthesis of N-aryldiazaspiro compounds. Thus, dianion of commercially available (Acros) ethyl 2-pyrrolidone-5-carboxylate can be alkylated with ethyl bromoacetate to generate ethyl 5-(carboethoxymethyl)-2-pyrrolidone-5-carboxylate. The second spiro ring can be formed by reacting ethyl 5-(carboethoxymethyl)-2-pyrrolidone-5-carboxylate with an arylamine. The resulting 2-aryl-2,6-diazaspiro[4.4]nonane-1,3,7-trione can be reduced with diborane to give 7-aryl-1,7-diazaspiro[4.4]nonane. Depending on the nature of the aryl group, the order of the synthetic steps can be changed.

Likewise, it can be necessary to incorporate protection/deprotection steps into particular methods.

A wide variety or arylamines are available for use in the approach outlined in Scheme 12. In addition to aminopyridines and aminopyrimidines, 3-aminoisoxazole is commercially available (Aldrich). This provides a means of synthesizing N-isoxazolyldiazaspiro compounds. The isomeric 4-aminoisoxazole can be made by reducing the corresponding nitro compound using the method described by Reiter, *J. Org. Chem.* 52: 2714 (1987). Examples of other amino derivatives of 5-membered aromatic rings include 3-aminoisothiazole, made according to Holland, et al., *J. Chem. Soc.*, 7277 (1965), and 4-aminoisothiazole, made according to Avalos, et al., *An. Quim.* 72: 922 (1976). Thus, a variety of N-aryldiazaspiro compounds of the present invention, in which the aryl group is a five-membered heterocycle, can be produced.

III. Pharmaceutical Compositions

The compounds described herein can be incorporated into pharmaceutical compositions and used to prevent a condition or disorder in a subject susceptible to such a condition or disorder, and/or to treat a subject suffering from the condition or disorder. The pharmaceutical compositions described herein include one or more compounds of Formulas I or II and/or pharmaceutically acceptable salts thereof. Optically active compounds can be employed as racemic mixtures or as pure enantiomers.

The manner in which the compounds are administered can vary. The compositions are preferably administered orally (e.g., in liquid form within a solvent such as an aqueous or non-aqueous liquid, or within a solid carrier). Preferred compositions for oral administration include pills, tablets, capsules, caplets, syrups, and solutions, including hard gelatin capsules and time-release capsules. Compositions may be formulated in unit dose form, or in multiple or subunit doses. Preferred compositions are in liquid or semisolid form. Compositions including a liquid pharmaceutically inert carrier such as water or other pharmaceutically compatible liquids or semisolids may be used. The use of such liquids and semisolids is well known to those of skill in the art.

The compositions can also be administered via injection, i.e., intraveneously, intramuscularly, subcutaneously, intraperitoneally, intraarterially, intrathecally; and intracerebroventricularly. Intravenous administration is a preferred method of injection. Suitable carriers for injection are well known to those of skill in the art, and include 5% dextrose solutions, saline, and phosphate buffered saline. The compounds can also be administered as an infusion or injection (e.g., as a suspension or as an emulsion in a pharmaceutically acceptable liquid or mixture of liquids).

The formulations may also be administered using other means, for example, rectal administration. Formulations useful for rectal administration, such as suppositories, are well known to those of skill in the art. The compounds can also be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); or transdermally (e.g., using a transdermal patch, using technology that is commercially available from Novartis and Alza Corporation). Although it is possible to administer the compounds in the form of a bulk active chemical, it is preferred to present each compound in the form of a pharmaceutical composition or formulation for efficient and effective administration.

Exemplary methods for administering such compounds will be apparent to the skilled artisan. The usefulness of these formulations may depend on the particular composition used and the particular subject receiving the treatment. These formulations may contain a liquid carrier that may be oily, aqueous, emulsified or contain certain solvents suitable to the mode of administration.

The compositions can be administered intermittently or at a gradual, continuous, constant or controlled rate to a warm-blooded animal (e.g., a mammal such as a mouse, rat, cat, rabbit, dog, pig, cow, or monkey), but advantageously are administered to a human being. In addition, the time of day and the number of times per day that the pharmaceutical formulation is administered can vary.

Preferably, upon administration, the active ingredients interact with receptor sites within the body of the subject that affect the functioning of the CNS. More specifically, in treating a CNS disorder, preferable administration is designed to optimize the effect upon those relevant receptor subtypes that have an effect upon the functioning of the CNS, while minimizing the effects upon muscle-type receptor subtypes. Other suitable methods for administering the compounds of the present invention are described in U.S. Pat. No. 5,604,231 to Smith et al.

Preferably, the compositions are administered such that active ingredients interact with regions where cytokine production is affected or occurs. The compounds described herein are very potent at treating these conditions or disorders (i.e., they affect cytokine production and/or secretion at very low concentrations) and are very efficacious (i.e., they inhibit cytokine production and/or secretion to a relatively high degree).

In certain circumstances, the compounds described herein can be employed as part of a pharmaceutical composition with other compounds intended to prevent or treat a particular disorder. In addition to effective amounts of the compounds described herein, the pharmaceutical compositions can also include various other components as additives or adjuncts. Exemplary pharmaceutically acceptable components or adjuncts which are employed in relevant circumstances include antioxidants, free-radical scavenging agents, peptides, growth factors, antibiotics, bacteriostatic agents, immunosuppressives, anticoagulants, buffering agents, anti-inflammatory agents, anti-pyretics, time-release binders, anaesthetics, steroids, vitamins, minerals and corticosteroids. Such components can provide additional therapeutic benefit, act to affect the therapeutic action of the pharmaceutical composition, or act towards preventing any potential side effects which can be imposed as a result of administration of the pharmaceutical composition.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder.

When treating a CNS disorder, an effective amount of compound is an amount sufficient to pass across the blood-brain barrier of the subject, to bind to relevant receptor sites in the brain of the subject and to activate relevant nicotinic receptor subtypes (e.g., provide neurotransmitter secretion, thus resulting in effective prevention or treatment of the disorder). Prevention of the disorder is manifested by delaying the onset of the symptoms of the disorder. Treatment of the disorder is manifested by a decrease in the symptoms associated with the disorder or an amelioration of the recurrence of the symptoms of the disorder. Preferably, the effective amount is sufficient to obtain the desired result, but insufficient to cause appreciable side effects.

The effective dose can vary, depending upon factors such as the condition of the patient, the severity of the symptoms of the disorder, and the manner in which the pharmaceutical composition is administered. For human patients, the effective dose of typical compounds generally requires administering the compound in an amount sufficient to activate relevant receptors to effect neurotransmitter (e.g., dopamine) release, but the amount should be insufficient to induce effects on skeletal muscles and ganglia to any significant degree. The effective dose of compounds will of course differ from patient to patient, but in general includes amounts starting where CNS effects or other desired therapeutic effects occur but below the amount where muscular effects are observed.

The compounds, when employed in effective amounts in accordance with the method described herein, are selective to certain relevant nicotinic receptors, but do not significantly activate receptors associated with undesirable side effects at concentrations at least greater than those required for eliciting the release of dopamine or other neurotransmitters. By this is meant that a particular dose of compound effective in preventing and/or treating a CNS disorder is essentially ineffective in eliciting activation of certain ganglionic-type nicotinic receptors at concentration higher than 5 times, preferably higher than 100 times, and more preferably higher than 1,000 times than those required for activation of dopamine release. This selectivity of certain compounds described herein against those ganglionic-type receptors responsible for cardiovascular side effects is demonstrated by a lack of the ability of those compounds to activate nicotinic function of adrenal chromaffin tissue at concentrations greater than those required for activation of dopamine release.

For human patients, the effective dose of typical compounds generally requires administering the compound in an amount of at least about 1, often at least about 10, and frequently at least about 25 $\mu$g/24 hr/patient. The effective dose generally does not exceed about 500, often does not exceed about 400, and frequently does not exceed about 300 $\mu$g/24 hr/patient. In addition, administration of the effective dose is such that the concentration of the compound within the plasma of the patient normally does not exceed 500 ng/mL and frequently does not exceed 100 ng/mL.

The compounds described herein, when employed in effective amounts in accordance with the methods described herein, can provide some degree of prevention of the progression of CNS disorders, ameliorate symptoms of CNS disorders, and ameliorate to some degree of the recurrence of CNS disorders. The effective amounts of those compounds are typically below the threshold concentration required to elicit any appreciable side effects, for example those effects relating to skeletal muscle. The compounds can be administered in a therapeutic window in which certain CNS disorders are treated and certain side effects are avoided. Ideally, the effective dose of the compounds described herein is sufficient to provide the desired effects upon the CNS but is insufficient (i.e., is not at a high enough level) to provide undesirable side effects. Preferably, the compounds are administered at a dosage effective for treating the CNS disorders but less than $\frac{1}{5}$, and often less than $\frac{1}{10}$, the amount required to elicit certain side effects to any significant degree.

Most preferably, effective doses are at very low concentrations, where maximal effects are observed to occur, with a minimum of side effects. Concentrations, determined as the amount of compound per volume of relevant tissue, typically provide a measure of the degree to which that compound affects cytokine production. Typically, the effective dose of such compounds generally requires administering the compound in an amount of less than 5 mg/kg of patient weight. Often, the compounds of the present invention are administered in an amount from less than about 1 mg/kg patent weight and usually less than about 100 $\mu$g/kg of patient weight, but frequently between about 10 $\mu$g to less than 100 $\mu$g/kg of patient weight. For compounds that do not induce effects on muscle-type nicotinic receptors at low concentrations, the effective dose is less than 5 mg/kg of patient weight; and often such compounds are administered in an amount from 50 $\mu$g to less than 5 mg/kg of patient weight. The foregoing effective doses typically represent that amount administered as a single dose, or as one or more doses administered over a 24-hour period.

For human patients, the effective dose of typical compounds generally requires administering the compound in an amount of at least about 1, often at least about 10, and frequently at least about 25 $\mu$g/24 hr/patient. For human patients, the effective dose of typical compounds requires administering the compound which generally does not exceed about 500, often does not exceed about 400, and frequently does not exceed about 300 $\mu$g/24 hr/patient. In addition, the compositions are advantageously administered at an effective dose such that the concentration of the compound within the plasma of the patient normally does not exceed 500 pg/mL, often does not exceed 300 pg/mL, and frequently does not exceed 100 pg/mL. When employed in such a manner, the compounds are dose dependent, and, as such, inhibit cytokine production and/or secretion when employed at low concentrations but do not exhibit those inhibiting effects at higher concentrations. The compounds exhibit inhibitory effects on cytokine production and/or secretion when employed in amounts less than those amounts necessary to elicit activation of relevant nicotinic receptor subtypes to any significant degree.

IV. Methods of Using the Compounds and/or Pharmaceutical Compositions

The compounds can be used to treat those types of conditions and disorders for which other types of nicotinic compounds have been proposed as therapeutics. See, for example, Williams et al., *Drug News Perspec.* 7(4):205 (1994), Arneric et al., *CNS Drug Rev.* 1(1):1 (1995), Arneric et al., *Exp. Opin. Invest. Drugs* 5(1):79 (1996), Bencherif et al., *J. Pharmacol. Exp. Ther.* 279:1413 (1996), Lippiello et al., *J. Pharmacol. Exp. Ther.* 279:1422 (1996), Damaj et al., *J. Pharmacol. Exp. Ther.* 291:390 (1999); Chiari et al., *Anesthesiology* 91:1447 (1999); Lavand'homme and Eisenbach, *Anesthesiology* 91:1455 (1999); *Neuroscience* (1997), Holladay et al., *J. Med. ChemChem.* 40(28):4169 (1997), Bannon et al., *Science* 279:77 (1998), PCT WO 94/08992, PCT WO 96/31475, and U.S. Pat. No. 5,583,140 to Bencherif et al., U.S. Pat. No. 5,597,919 to Dull et al., and U.S. Pat. No. 5,604,231 to Smith et al., the disclosures of which are incorporated herein by reference in their entirety.

The compounds can also be used as adjunct therapy in combination with existing therapies in the management of the aforementioned types of diseases and disorders. In such situations, it is preferably to administer the active ingredients to in a manner that optimizes effects upon abnormal cytokine production, while minimizing effects upon receptor subtypes such as those that are associated with muscle and ganglia. This can be accomplished by targeted drug delivery and/or by adjusting the dosage such that a desired effect is obtained without meeting the threshold dosage required to achieve significant side effects.

Treatment of CNS Disorders

The compounds described herein are effective at treating a wide variety of CNS disorders. Examples of CNS disorders that can be treated in accordance with the present invention include pre-senile dementia (early onset Alzheimer's disease), senile dementia (dementia of the Alzheimer's type), Lewy Body dementia, HIV-dementia, multiple cerebral infarcts, Parkinsonism including Parkinson's disease, Pick's disease, Huntington's chorea, tardive dyskinesia, hyperkinesia, mania, attention deficit disorder, anxiety, depression, mild cognitive impairment, dyslexia, schizophrenia and Tourette's syndrome.

CNS Disorders can be treated and/or prevented by administering to a patient an amount of a compound or pharmaceutical composition effective for providing some degree of prevention of the progression of a CNS disorder (i.e., provide protective effects), amelioration of the symptoms of a CNS disorder, and amelioration of the recurrence of a CNS disorder. The method involves administering an effective amount of a compound selected from the general formulae, which are set forth hereinbefore.

Other Disorders

In addition to treating CNS disorders, the pharmaceutical compositions can be used to prevent or treat certain other conditions, diseases and disorders. Examples include neurodegenerative diseases, autoimmune disorders such as Lupus, disorders associated with cytokine release, anti-inflammatory uses, as well as those indications set forth in PCT WO 98/25619. The pharmaceutical compositions can ameliorate many of the symptoms associated with those conditions, diseases and disorders.

Inhibition of cytokine release is desirable in the treatment of cachexia, inflammation, neurodegenerative diseases, viral infection, and neoplasia. The cachexia is often secondary to infection (e.g., as occurs in AIDS, AIDS-related complex and neoplasia) or to cancer therapy. Examples of inflammatory disorders that can be treated include acute cholangitis, aphthous stomatitis, asthma, ulcerative colitis, inflammatory bowel disease, pouchitis, viral pneumonitis and arthritis (e.g., rheumatoid arthritis and osteoarthritis).

The pharmaceutical compositions can also be used as anti-infectious agents (e.g, for treating bacterial, fungal and viral infections, as well as the effects, such as sepsis, of other types of toxins).

The compounds can be used as analgesics, to treat convulsions such as those that are symptomatic of epilepsy, to treat conditions such as syphillis and Creutzfeld-Jakob disease.

The compounds can also be appropriately synthesized and used as or within pharmaceutical compositions that are used as diagnostic probes.

The compounds useful according to the method of the present invention have the ability to bind to, and in most circumstances, cause activation of, nicotinic cholinergic receptors of the brain of the patient (e.g., such as those receptors that modulate dopamine release). As such, such compounds have the ability to express nicotinic pharmacology, and in particular, to act as nicotinic agonists. The receptor binding constants of typical compounds useful in carrying out the present invention generally exceed about 0.1 nM, often exceed about 1 nM, and frequently exceed about 10 nM. The receptor binding constants of such typical compounds generally are less than about 1 $\mu$M often are less than about 100 nM, and frequently are less than about 50 nM. Receptor binding constants provide a measure of the ability of the compound to bind to half of the relevant receptor sites of certain brain cells of the patient. See, Cheng, et al., Biochem. Pharmacol. 22: 3099 (1973). The compounds useful according to the method of the present invention have the ability to demonstrate a nicotinic function by effectively eliciting ion flux through, and/or neurotransmitter secretion from, nerve ending preparations (e.g., thalamic or striatal synaptosomes). As such, such compounds have the ability to cause relevant neurons to become activated, and to release or secrete acetylcholine, dopamine, or other neurotransmitters. Generally, typical compounds useful in carrying out the present invention effectively provide for relevant receptor activation in amounts of at least about 30 percent, often at least about 50 percent, and frequently at least about 75 percent, of that maximally provided by (S)-(−)-nicotine. Generally, typical compounds useful in carrying out the present invention are more potent than (S)-(−)-nicotine in eliciting relevant receptor activation. Generally, typical compounds useful in carrying out the present invention effectively provide for the secretion of dopamine in amounts of at least about 50 percent, often at least about 75 percent, and frequently at least about 100 percent, of that maximally provided by (S)-(−)-nicotine. Certain compounds of the present invention can provide secretion of dopamine in an amount which can exceed that maximally provided by (S)-(−)-nicotine. Generally, typical compounds useful in carrying out the present invention are less potent than (S)-(−)-nicotine in eliciting neurotransmitter secretion, such as dopamine secretion.

The compounds of the present invention, when employed in effective amounts in accordance with the method of the present invention, lack the ability to elicit activation of nicotinic receptors of human muscle to any significant degree. In that regard, the compounds of the present invention demonstrate poor ability to cause isotopic rubidium ion flux through nicotinic receptors in cell preparations expressing muscle-type nicotinic acetylcholine receptors. Thus, such compounds exhibit receptor activation constants or EC50 values (i.e., which provide a measure of the concentration of compound needed to activate half of the relevant receptor sites of the skeletal muscle of a patient) which are extremely high (i.e., greater than about 100 $\mu$M). Generally, typical preferred compounds useful in carrying the present invention activate isotopic rubidium ion flux by less than 10 percent, often by less than 5 percent, of that maximally provided by S(−) nicotine.

The compounds of the present invention, when employed in effective amounts in accordance with the method of the present invention, are selective to certain relevant nicotinic receptors, but do not cause significant activation of receptors associated with undesirable side effects. By this is meant that a particular dose of compound resulting in prevention and/or treatment of a CNS disorder, is essentially ineffective in eliciting activation of certain ganglionic-type nicotinic receptors. This selectivity of the compounds of the present invention against those receptors responsible for cardiovascular side effects is demonstrated by a lack of the ability of those compounds to activate nicotinic function of adrenal chromaffin tissue. As such, such compounds have poor ability to cause isotopic rubidium ion flux through nicotinic receptors in cell preparations derived from the adrenal gland. Generally, typical preferred compounds useful in carrying out the present invention activate isotopic rubidium ion flux by less than 10 percent, often by less than 5 percent, of that maximally provided by S(−) nicotine.

Compounds of the present invention, when employed in effective amounts in accordance with the method of the present invention, are effective towards providing some degree of prevention of the progression of CNS disorders, amelioration of the symptoms of CNS disorders, and amelioration to some degree of the recurrence of CNS disorders. However, such effective amounts of those compounds are not sufficient to elicit any appreciable side effects, as is demonstrated by decreased effects on preparations believed to reflect effects on the cardiovascular system, or effects to skeletal muscle. As such, administration of compounds of the present invention provides a therapeutic window in which treatment of certain CNS disorders is provided, and side effects are avoided. That is, an effective dose of a compound of the present invention is sufficient to provide the desired effects upon the CNS, but is insufficient (i.e., is not at a high enough level) to provide undesirable side effects. Preferably, effective administration of a compound of the present invention resulting in treatment of CNS disorders occurs upon administration of less ⅓, frequently less than ⅕, and often less than ¹⁄₁₀, that amount sufficient to cause any side effects to a significant degree.

The following examples are provided to illustrate the present invention, and should not be construed as limiting thereof. In these examples, all parts and percentages are by weight, unless otherwise noted. Reaction yields are reported in mole percentages. Several commercially available starting materials are used throughout the following examples. 3-Bromopyridine, 3,5-dibromopyridine, 5-bromonicotinic acid, 5-bromopyrimidine, and 4-penten-2-ol were obtained from Aldrich Chemical Company or Lancaster Synthesis Inc. 2-Amino-5-bromo-3-methylpyridine was purchased from Maybridge Chemical Company Ltd. (R)-(+)-propylene oxide was obtained from Fluka Chemical Company, and (S)-(−)-propylene oxide was obtained from Aldrich Chemical Company. Column chromatography was done using either Merck silica gel 60 (70–230 mesh) or aluminum oxide (activated, neutral, Brockmann I, standard grade, about 150 mesh). Pressure reactions were done in a heavy wall glass pressure tube (185 mL capacity), with Ace-Thread, and plunger valve available from Ace Glass Inc. Reaction mixtures were typically heated using a high-temperature silicon oil bath, and temperatures refer to those of the oil bath. The following abbreviations are used in the following examples: $CHCl_3$ for chloroform, $CH_2Cl_2$ for dichloromethane, $CH_3OH$ for methanol, DMF for N,N-dimethylformamide, and EtOAc for ethyl acetate, THF for tetrahydrofuran, and $Et_3N$ for triethylamine.

V. Assays

Binding Assay

The ability of the compounds to bind to relevant receptor sites was determined in accordance with the techniques described in U.S. Pat. No. 5,597,919 to Dull et al. Inhibition constants ($K_i$ values) were calculated from the $IC_{50}$ values using the method of Cheng et al., *Biochem. Pharmacol.* 22:3099 (1973). For the α4β2 subtype, the Ki value for each of the examples in this application was less than 1 μM, indicating that compounds of the present invention bind tightly to the receptor.

Determination of Log P Value

Log P values, which have been used to assess the relative abilities of compounds to pass across the blood-brain barrier (Hansch, et al., *J. Med. Chem.* 11: 1 (1968)), were calculated using the Cerius$^2$ software package Version 3.5 by Molecular Simulations, Inc.

Determination of Dopamine Release

Dopamine release was measured using the techniques described in U.S. Pat. No. 5,597,919 to Dull et al. Release is expressed as a percentage of release obtained with a concentration of (S)-(−)-nicotine resulting in maximal effects. Reported $EC_{50}$ values are expressed in nM, and $E_{max}$ values represent the amount released relative to (S)-(−)-nicotine on a percentage basis.

Determination of Rubidium Ion Release

Rubidium release was measured using the techniques described in Bencherif et al., *JPET* 279: 1413–1421 (1996). Reported $EC_{50}$ values are expressed in nM, and $E_{max}$ values represent the amount of rubidium ion released relative to 300 μM tetramethylammonium ion, on a percentage basis.

Determination of Interaction with Muscle Receptors

The determination of the interaction of the compounds with muscle receptors was carried out in accordance with the techniques described in U.S. Pat. No. 5,597,919 to Dull et al. The maximal activation for individual compounds ($E_{max}$) was determined as a percentage of the maximal activation induced by (S)-(−)-nicotine. Reported $E_{max}$ values represent the amount released relative to (S)-(−)-nicotine on a percentage basis.

Determination of Interaction with Ganglion Receptors

The determination of the interaction of the compounds with ganglionic receptors was carried out in accordance with the techniques described in U.S. Pat. No. 5,597,919 to Dull et al. The maximal activation for individual compounds ($E_{max}$) was determined as a percentage of the maximal activation induced by (S)-(−)-nicotine. Reported $E_{max}$ values represent the amount released relative to (S)-(−)-nicotine on a percentage basis.

Selectivity

The selectivity of the compounds for a given receptor can be evaluated by comparing the binding of the compounds to different receptors using known methodology.

VI. Synthetic Examples

The following synthetic examples are provided to illustrate the present invention and should not be construed as limiting the scope thereof. In these examples, all parts and percentages are by weight, unless otherwise noted. Reaction yields are reported in mole percentage.

EXAMPLE 1

Sample No. 1 is 7-(3-pyridyl)-1,7-diazaspiro[4.4]nonane dihydrochloride, which was prepared according to the following techniques:

Nitroethylene

Nitroethylene was prepared accordingly to the procedure reported by Ranganathan, et al., *J. Org. Chem.* 45: 1185 (1980).

Ethyl 2-(2-nitroethyl)-1-benzylpyrrolidine-2-carboxylate

Under a nitrogen atmosphere, a solution of diisopropylamine (4.34 g, 6.01 mL, 42.9 mmol) in dry THF (50 mL) was cooled in an ice bath as n-butyllithium (17.1 mL of 2.5 M in hexane, 42.8 mmol) was added by syringe. The ice bath was removed and the solution of lithium diisopropylamide was first warmed to ambient temperature and then transferred by cannula into a stirred solution of ethyl (S)-N-benzyl pyrrolidine-2-carboxylate (10.0 g, 42.9 mmol) (Fluka) in dry THF (50 mL), held at −78° C. under nitrogen. The addition took 10 min. After stirring an additional 30 min at −78° C., the enolate solution was treated (via cannula) with a solution of nitroethylene (3.13 g, 42.9 mmol) in dry THF (20 mL). The mixture was then stirred for 1 h at −78° C. Saturated aqueous ammonium chloride solution was then added (at −78° C.), and the mixture was warmed to ambient temperature and extracted the ethyl acetate (4×30 mL). The extracts were dried ($K_2CO_3$) and concentrated by rotary evaporation. The residue was purified by chromatography on a Merck silica gel 60 (70–230 mesh) column with 9:1

(v/v) hexane/ethyl acetate. Concentration of selected fractions gave 10.0 g (76.3%) of viscous, tan oil.

6-Benzyl-2,6-diazaspiro[4.4]nonan-1-one

Raney nickel (~2 g) was added to a solution of ethyl 2-(2-nitroethyl)-1-benzylpyrrolidine-2-carboxylate (6.00 g, 19.6 mmol) in absolute ethanol (200 mL) in a hydrogenation bottle. The mixture was shaken for 12 h under a hydrogen atmosphere (50 psi) in a Parr hydrogenation apparatus, filtered through a Celite pad and concentrated by rotary evaporation. GCMS analysis indicated that the hydrogenation product was a mixture of the primary amine and the lactam resulting from cyclization of the amine onto the ester. The mixture was dissolved in toluene (150 mL). A catalytic amount of p-toluenesulfonic acid (~30 mg) was added and the mixture was heated at reflux under a nitrogen atmosphere for 24 h. Upon evaporation of the toluene, the residue (now entirely lactam, by GCMS) crystallized to give 4.20 g (93.1%) of tan solid (mp 152–153° C.).

1-Benzyl-1,7-diazaspiro[4.4]nonane

Lithium aluminum hydride (1.98 g, 52.2 mmol) was added in portions, under argon, to a ice bath cooled solution of 6-benzyl-2,6-diazaspiro[4.4]nonan-1-one (4.00 g, 17.4 mmol) in dry THF (100 mL). The addition funnel was replaced with a reflux condenser, and the mixture was heated at reflux for 24 h. The mixture was cooled to 0° C. and treated drop-wise (caution: exothermic reaction) with 10 M aqueous sodium hydroxide until hydrogen evolution ceased and the aluminate salts were granular. The mixture was stirred 1 h at 0° C. and filtered through Celite. The filtrate was dried ($K_2CO_3$) and concentrated, leaving 3.60 g (95.7%) of viscous, colorless liquid.

1-Benzyl-7-(3-pyridyl)-1,7-diazaspiro[4.4]nonane

A mixture of 1-benzyl-1,7-diazaspiro[4.4]nonane (2.00 g, 9.26 mmol), 3-bromopyridine (1.38 g, 8.73 mmol), potassium tert-butoxide (2.50 g, 22.3 mmol), tris(dibenzylideneacetone)dipalladium(0) (0.318 g, 0.347 mmol), 2,2'-bis(diphenylphosphino)-1,1'-binaphthyl (0.324 g, 0.520 mmol) and dry toluene (50 mL) was placed in a pressure tube under argon. The mixture was stirred and heated at 90° C. (bath temperature) for 24 h and cooled. Water (20 mL) was added and the mixture was extracted with ethyl acetate (6×25 mL). The extracts were dried ($K_2CO_3$) and concentrated. Column chromatography of the residue on Merck silica gel 60 (70–230 mesh), with 6:4 (v/v) chloroform/acetone, gave 1.80 g (66.2%) of light brown oil, after concentration of selected fractions.

7-(3-Pyridyl)-1,7-diazaspiro[4.4]nonane dihydrochloride

Aqueous hydrochloric acid (0.5 mL of 12 M) and 10% palladium on carbon (0.100 g) were added to a solution of 1-benzyl-7-(3-pyridyl)-1,7-diazaspiro[4.4]nonane (1.0 g, 3.41 mmol) in methanol (30 mL). The mixture was shaken under a hydrogen atmosphere (50 psi) in a Parr hydrogenation apparatus for 24 h and filtered through Celite. The filtrate was concentrated by rotary evaporation and column chromatographed on Merck silica gel 60 (70–230 mesh). Elution with 0.01:1:9 (v/v) aqueous ammonia/methanol/chloroform, and concentration of selected fractions, gave 0.650 g (93.8%) of viscous, brown oil. A portion (300 mg, 1.48 mmol) of this material was treated with aqueous hydrochloric acid (2 mL). The water was azeotropically removed by repeated treatment with small volumes of ethanol (~5 mL) and rotary evaporation. The resulting solid was recrystallized from hot isopropanol to give 360 mg (88.2%) of fine tan crystals.

EXAMPLE 2

Sample 2 is 1-(3-pyridyl)-1,7-diaza-spiro[4.4]nonane dihydrochloride, which was prepared according to the following techniques:

tert-Butyl 6-benzyl-2,6-diazaspiro[4.4]nonane-2-carboxylate

Di-t-butyl dicarbonate (1.45 g, 6.64 mmol) was added to a solution of 1-benzyl-1,7-diazaspiro[4.4]nonane (1.30 g, 6.01 mmol) and triethylamine (1 mL) in dichloromethane (25 mL), and the mixture was stirred at ambient temperature overnight. The mixture was poured into saturated aqueous sodium bicarbonate (10 mL) and extracted with chloroform (4×25 mL). The extracts were dried ($K_2CO_3$) and concentrated by rotary evaporation. The residue was column chromatographed on Merck silica gel 60 (70–230 mesh), eluting with, to give 1.85 g (97.4%) of viscous, colorless oil, after concentration of selected fractions.

tert-Butyl 2,6-diazaspiro[4.4]nonane-2-carboxylate

A solution of t-butyl 6-benzyl-2,6-diazaspiro[4.4]nonane-2-carboxylate (1.70 g, 5.37 mmol) in methanol (30 mL) was mixed with 10% palladium on carbon (50 mg). The mixture was shaken under a hydrogen atmosphere (50 psi) in a Parr hydrogenation apparatus for 8 h and filtered through Celite. The filtrate was concentrated by rotary evaporation and high vacuum treatment, leaving 1.26 g of viscous, light brown oil (>100%), which was of sufficient purity to be used in the subsequent reaction.

tert-Butyl 6-(3-pyridyl)-2,6-diazaspiro[4.4]nonane-2-carboxylate

A mixture of tert-butyl 2,6-diazaspiro[4.4]nonane-2-carboxylate (1.00 g, ~4.4 mmol), 3-bromopyridine (0.736 g, 4.66 mmol), potassium tert-butoxide (1.22 g, 10.9 mmol), tris(dibenzylideneacetone)dipalladium(0) (0.155 g, 0.169 mmol), 2,2'-bis(diphenylphosphino)-1,1'-binaphthyl (0.158 g, 0.254 mmol) and dry toluene (25 mL) was placed in a pressure tube under argon. The mixture was stirred and heated at 180° C. (bath temperature) for 8 h and cooled. Thin layer analysis indicated that very little conversion had taken place. A second charge, equal in quantity to the first, of all reagents except the tert-butyl 2,6-diazaspiro[4.4]nonane-2-carboxylate was added to pressure tube and the tube was returned to the bath for another 8 h. Again relatively little reaction seemed to have occurred, so a third charge of reagents was added and heating (at 180° C.) was continued for a third 8 h period. Water (20 mL) was added and the mixture was extracted with ethyl acetate (6×25 mL). The extracts were dried ($K_2CO_3$) and concentrated. Column chromatography of the residue on Merck silica gel 60 (70–230 mesh), with 6:4 (v/v) chloroform/acetone, gave 150 mg (~11%) of light brown oil, after concentration of selected fractions.

1-(3-Pyridyl)-1,7-diazaspiro[4.4]nonane dihydrochloride

A solution of tert-butyl 6-(3-pyridyl)-2,6-diazaspiro[4.4]nonane-2-carboxylate (100 mg, 0.330 mmol) in dichloromethane (5 mL) was rapidly stirred with 1 mL of 12 M hydrochloric acid at ambient temperature for 1 h, during which time the biphasic mixture became monophasic. The dichloromethane was evaporated, and the residue was dissolved in water (3 mL) and made strongly basic (pH 9) with potassium carbonate. The mixture was saturated with sodium chloride and extracted with chloroform (4×10 mL). The extracts were dried ($K_2CO_3$) and concentrated, first by rotary evaporation and then by high vacuum treatment. The viscous brown oil which resulted was 98% pure by GCMS and weighed 50 mg (73%). A sample of this free base (40 mg, 020 mmol)was dissolved in 10 drops of 12 M hydrochloric acid. The water was azeotropically removed by repeated treatment with small volumes of ethanol (~5 mL) and rotary evaporation. The resulting solid was recrystallized from hot isopropanol to give 40 mg (72%) of fine tan crystals (mp 170–175° C.).

EXAMPLE 3

Sample 3 is 1-methyl-7-(3-pyridyl)-1,7-diazaspiro[4.4]nonane, which was prepared according to the following techniques:

1-Methyl-7-(3-pyridyl)-1,7-diazaspiro[4.4]nonane 7-(3-Pyridyl)-1,7-diazaspiro[4.4]nonane (30 mg, 0.15 mmol) was dissolved in 98% formic acid (0.5 mL) and formaldehyde (1 mL, 28% aqueous solution). The reaction mixture was heated to reflux for 8 h. The reaction mixture was cooled to room temperature, basified with saturated aqueous sodium bicarbonate to pH 9–10 and extracted with chloroform (4×3 mL). The combined chloroform extracts were dried ($K_2CO_3$), filtered and concentrated on a rotary evaporator to afford 30 mg of the desired compound (93.6%) as a light brown liquid.

EXAMPLE 4

Sample 4 is 1-methyl-7-(5-ethoxy-3-pyridyl)-1,7-diazaspiro[4.4]nonane, which was prepared according to the following techniques:

5-bromo-3-ethoxypyridine

Under a nitrogen atmosphere, sodium (4.60 g, 200 mmol) was added to absolute ethanol (100 mL) at 0–5° C., and the stirring mixture was allowed to warm to ambient temperature over 18 h. To the resulting solution was added 3,5-dibromopyridine (31.5 g, 133 mmol), followed by DMF (100 mL). The mixture was heated at 70° C. for 48 h. The brown mixture was cooled, poured into water (600 mL), and extracted with ether (3×500 mL). The combined ether extracts were dried ($Na_2SO_4$), filtered, and concentrated by rotary evaporation. Purification by vacuum distillation afforded 22.85 g (85.0%) of an oil, bp 89–90° C. at 2.8 mm Hg (lit. bp 111° C. at 5 mm Hg, see K. Clarke, et al., *J. Chem. Soc.* 1885 (1960)).

1-Benzyl-7-(5-ethoxy-3-pyridyl)-1,7-diazaspiro[4.4]nonane

1-Benzyl-1,7-diazaspiro[4.4]nonane (500.0 mg, 2.4 mmol) was dissolved in dry toluene (15 mL) in a 50 mL round bottom flask equipped with a magnetic stirring bar. Nitrogen was bubbled through the solution in a slow stream. To the stirring solution was added 3-bromo-5-ethoxypyridine (513.8 mg, 2.55 mmol), potassium tert-butoxide (1039.0 mg, 9.26 mmol), rac-2,2'-bis(diphenylphosphino)-1,1'-binaphthyl (86.4 mg, 0.14 mmol) and tris(dibenzylideneacetone)dipalladium(0) (63.6 mg, 0.06 mmol), while continuing to purge with nitrogen. Nitrogen flow was discontinued and the flask was sealed and heated at 90° C. for 8 h. The reaction was cooled and the solvent was removed by rotary evaporation. The resulting residue was suspended in saturated aqueous sodium bicarbonate (10 mL) and extracted with chloroform (4×25 mL). The combined organic extracts were dried ($Na_2SO_4$), filtered, and concentrated by rotary evaporation to a thick dark mass. Purification by column chromatography, using methanol/chloroform (2:98, v/v) as the eluent, gave 0.54 g of the desired compound as a light brown viscous liquid (69%).

7-(5-Ethoxy-3-pyridyl)-1,7-diazaspiro[4.4]nonane

To a solution of 1-benzyl-7-(5-ethoxy-3-pyridyl)-1,7-diazaspiro[4.4]nonane (540 mg, 1.6 mmol) in ethanol (25 mL) in a pressure bottle was added concentrated HCl (1 mL) and Pearlman's catalyst ($Pd(OH)_2$, 20% on carbon, 50 mg). The solution was shaken under 50 psi of hydrogen gas for 8 h. The catalyst was removed by filtration through Celite, and the filter cake was washed with ethanol (20 mL). The solvent was removed by rotary evaporation, and the residue was basified with saturated aqueous sodium bicarbonate to pH 8–9. Solid sodium chloride (2 g) was added, and the mixture was extracted with chloroform (4×20 mL). The combined chloroform extracts were dried ($Na_2SO_4$), filtered and concentrated by rotary evaporation to afford 360.7 mg of the desired compound as a light brown viscous liquid (91.1%).

1-Methyl-7-(5-ethoxy-3-pyridyl)-1,7-diazaspiro[4.4]nonane

To a stirring solution of 7-(5-ethoxy-3-pyridyl)-1,7-diazaspiro[4.4]nonane (360.4 mg, 1.4 mmol) in 37% aqueous solution of formaldehyde (4 mL) was added 98% formic acid (2 mL) under nitrogen. The reaction mixture was heated to reflux for 8 h. The reaction mixture was cooled to room temperature, then basified with saturated aqueous sodium bicarbonate to pH 8–9 and extracted with chloroform (4×15 mL). The combined chloroform extracts were dried ($Na_2SO_4$), filtered and concentrated by rotary evaporation to afford a viscous brown liquid. This was distilled using a Kugelrohr apparatus (2 mm, 180° C.) to give a very light cream-colored syrup (340 mg, 89.3%).

EXAMPLE 5

Sample 5 is 1-methyl-7-(5-phenoxy-3-pyridyl)-1,7-diazaspiro[4.4]nonane, which was prepared according to the following techniques:

3-Bromo-5-phenoxypyridine

Sodium hydride (1.35 g of 80% in mineral oil, 45.0 mmol) was added to a stirred solution of phenol (4.26 g, 45.3 mmol) in DMF (30 mL) at 0° C., under nitrogen. The mixture was stirred at room temperature for 3 h, treated with 3,5-dibromopyridine (4.0 g, 16.9 mmol) and heated at 100° C. for 48 h. The reaction mixture was cooled to room temperature, poured into a mixture of water (100 mL) and 5M sodium hydroxide (10 mL), and extracted with ether (3×60 mL). The combined ether extracts were dried ($Na_2SO_4$), filtered, and rotary evaporated to a pale yellow semi-solid (4.9 g). This was chromatographed on a silica gel (200 g) column with hexane/ethyl acetate/chloroform (8:1:1, v/v) as eluant to give 2.86 g (68% yield) of a colorless oil.

1-Benzyl-7-(5-phenoxy-3-pyridyl)-1,7-diazaspiro 14.41 nonane

1-Benzyl-1,7-diazaspiro[4.4]nonane (500.0 mg, 2.4 mmol) was dissolved in dry toluene (15 mL) in a 50 mL round bottom flask equipped with a magnetic stirring bar. Nitrogen was bubbled through the solution in a slow stream. To the stirring solution was added 3-bromo-5-phenoxypyridine (636.8 mg, 2.55 mmol), potassium tert-butoxide (1039.0 mg, 9.26 mmol), rac-2,2'-bis(diphenylphosphino)-1,1'-binaphthyl (86.4 mg, 0.14 mmol) and tris(dibenzylideneacetone)dipalladium(0) (63.6 mg, 0.06 mmol), while continuing to purge with nitrogen. Nitrogen flow was discontinued and the flask was sealed and heated at 90° C. for 8 h. The reaction was cooled and the solvent was removed by rotary evaporation. The resulting residue was suspended in saturated aqueous sodium bicarbonate (10 mL) and extracted with chloroform (4×25 mL). The combined organic extracts were dried ($Na_2SO_4$), filtered, concentrated by rotary evaporation to a thick dark mass. This was purified by column chromatography, using methanol/chloroform (2:98, v/v) as the eluent, to afford 0.70 g of the desired compound as a light brown viscous liquid (78.6%).

7-(5-Phenoxy-3-pyridyl)-1,7-diazaspiro[4,4]nonane

To a solution of 1-benzyl-7-(5-phenoxy-3-pyridyl)-1,7-diazaspiro[4.4]nonane (690 mg, 1.79 mmol) in ethanol (25 mL) in a pressure bottle was added concentrated HCl (1 mL) and Pearlman's catalyst ($Pd(OH)_2$, 20% on carbon, 50 mg). The solution was shaken under 50 psi of hydrogen gas for 8 h. The catalysts was removed by filtration through Celite, and the filter cake was washed with ethanol (20 mL). The solvent was removed by rotary evaporation, and the residue was basified with saturated aqueous sodium bicarbonate to pH 8–9. Solid sodium chloride (2 g) was added, and the solution was extracted with chloroform (4×20 mL). The combined chloroform extracts were dried ($Na_2SO_4$), filtered and concentrated by rotary evaporation to afford 490 mg of the desired compound as a light brown viscous liquid (92.7%).

1-Methyl-7-(5-phenoxy-3-pyridyl)-1,7-diazaspiro[4.4]nonane

To a stirring solution of 7-(5-phenoxy-3-pyridyl)-1,7-diazaspiro[4.4]nonane (420 mg, 1.42 mmol) in 37% aqueous solution of formaldehyde (5 mL) was added 98% formic acid (3 mL) under nitrogen. The reaction mixture was heated to reflux for 8 h. The reaction mixture was cooled to room temperature, then basified with saturated aqueous sodium bicarbonate to pH 8–9 and extracted with chloroform (4×15 mL). The combined chloroform extracts were dried ($Na_2SO_4$), filtered and concentrated by rotary evaporation to afford a thick brown viscous liquid. This was distilled using a Kugelrohr apparatus (2 mm, 180° C.) to give a very pale cream-colored syrup (400 mg, 90.9%).

1-Methyl-7-(5-phenoxy-3-pyridyl)-1,7-diazaspiro[4.4]nonane dihydrochloride

1-Methyl-7-(5-phenoxy-3-pyridyl)-1,7-diazaspiro[4.4]nonane (200-mg, 0.65 mmol) was dissolved in concentrated HCl (1 mL) and sonicated for 5 min. The excess acid and water were removed by repeated azeotropic evaporation with small portions of ethanol. A pale yellow solid was obtained. The solid was dissolved in the minimum amount of absolute ethanol (~1 mL), and then ether was added drop-wise until the solution became opaque. Cooling in the refrigerator overnight produced cream-colored crystals, which were filtered, washed with ether and dried in a vacuum oven to yield 210 mg (85.4%) of pure dihydrochloride salt, m.p. 180–191° C.

EXAMPLE 6

Sample 6 is 1'-(3-pyridyl)-spiro[1-azabicyclo[2.2.1]heptane-2,3'-pyrrolidine] dihydrochloride, which was prepared according to the following techniques:

(3-oxolanyl)methyl methanesulfonate

To a stirring solution of (3-oxolanyl)methan-1-ol (25 g, 245 mmol) and triethylamine (34.37 mL, 245 mmol) in dry dichloromethane (250 mL) at 0° C. under $N_2$ atmosphere was added dropwise methanesulfonyl chloride (18.94 mL, 245 mmol). The reaction mixture was stirred overnight after warming to room temperature, then a saturated solution of $NaHCO_3$ (100 mL) was added and the mixture stirred for another 30 min. The biphasic mixture was separated and the organic layer was discarded. The aqueous layer was extracted with dichloromethane (3×25 mL) and the combined dichloromethane extracts were dried ($Na_2SO_4$), filtered and concentrated by rotary evaporation to give 42.16 g of (3-oxolanyl)methyl methanesulfonate (99%) as a light brown liquid.

3-(Bromomethyl)oxolane

To a stirring solution of (3-oxolanyl)methyl methanesulfonate (42.16 g, 239.5 mmol) in dry acetone (600 mL) was added lithium bromide (101.7 g, 1198 mmol). The reaction mixture was heated to reflux for 3 h, then it was cooled and the solvent removed by rotary evaporation. The residue was dissolved in water (200 mL) and extracted with dichloromethane (2×100 mL). The combined extracts were dried ($Na_2SO_4$), filtered and concentrated by rotary evaporation to afford a light brown liquid. It was distilled at 70° C. and 1 mm of pressure to give 33.00 g (86.77%) of 3-(bromomethyl)oxolane as a colorless liquid.

Methyl 3-aza-4,4-diphenyl-but-3-enoate

To a stirring solution of methyl glycine ester hydrochloride (17.49 g, 139 mmol) in dry dichloromethane (150 mL) under $N_2$ at room temperature was added diphenylimine (25.00 g, 137 mmol) in one portion. The reaction mixture was stirred for 24 h, during which time ammonium chloride precipitated. Water (20 mL) was added and the layers were separated. The organic layer was washed with saturated $Na_2CO_3$ solution (2×20 mL) and brine (20 mL). The organic layer was dried ($Na_2SO_4$), filtered and concentrated by rotary evaporation to give 35 g of a thick light brown syrup (99% pure) in ~100% yield. This was taken on to the next reaction without further purification.

Methyl 3-(3-oxolanyl)-2-aminopropanoate

To a stirring solution of methyl 3-aza-4,4-diphenyl-but-3-enoate (23.00 g, 90 mmol) under $N_2$ in dry DMF (25 mL) and toluene (25 mL) was added potassium tert-butoxide (10.20 g, 90 mmol) in one portion. The reaction mixture was stirred for 15 min; it changed color from yellow to dark reddish-brown. Then, a solution of 3-(bromomethyl)oxolane (15 g, 90 mmol) in DMF (20 mL) and dry toluene (20 mL) was added via cannula over a period of 30 min. The reaction mixture was stirred for an additional 16 h at ambient temperature. Then, 1N HCl (100 mL) was added to the reaction mixture and it was stirred for another 30 min. The mixture was extracted with ethyl acetate (3×50 mL). The aqueous layer was basified with solid $K_2CO_3$ to pH 8–9, then saturated with solid NaCl and extracted with ethyl acetate (4×50 mL). The combined ethyl acetate extracts were dried ($K_2CO_3$), filtered and concentrated by rotary evaporation to give methyl 3-(3-oxolanyl)-2-aminopropanoate (10 g, 59.37%) as a brown liquid.

Ethyl 1-azabicyclo[2.2.1]heptane-2-carboxylate

Methyl 3-(3-oxolanyl)-2-aminopropanoate (6.00 g, 3.46 mmol) was placed in a sealed pressure tube, then 48% aqueous HBr (20 mL) was added and the solution was saturated with HBr gas. The tube was sealed carefully and heated at 110–120° C. for 8 h. The reaction was then cooled and the contents transferred to a 250 mL round bottom flask with 20 mL of water. The excess acid was removed by rotary evaporation to give a semi solid brown mass. Then 30% aqueous ammonium hydroxide (150 mL) was added at 0° C. and the mixture was heated at gentle reflux for 4 h. The solvent was removed by rotary evaporation to give a brown solid, which then was dissolved in absolute ethanol (50 mL). Concentrated $H_2SO_4$ (10 mL) was added and the solution was refluxed for 8 h. The contents were cooled in an ice bath, and then basified with concentrated $NaHCO_3$ solution to pH 8–9 and extracted with chloroform (4×40 mL). The combined chloroform extracts were dried ($K_2CO_3$), filtered and concentrated to give a brown-black liquid which was distilled using a Kugelrohr apparatus (1 mm, 140° C.) to afford a colorless liquid (4 g, 68.25%) as a mixture of the exo and endo isomers of ethyl 1-azabicyclo[2.2.1]heptane-2-carboxylate.

Ethyl 1-aza-2-(nitroethyl)bicyclo[2.2.1]heptane-2-carboxylate

Lithium diisopropylamide (LDA) was prepared at 0° C. from diisopropylamine (2.078 g, 20.53 mmol) and n-butyllithium (8.21 mL, 20.53 mmol) in dry THF (20 mL) under an $N_2$ atmosphere. To a stirring solution of a mixture of the exo and endo isomers of ethyl 1-azabicyclo[2.2.1]heptane-2-carboxylate (2.67 g, 15.79 mmol) in dry THF (35 mL) at −78° C. under $N_2$ atmosphere was added via cannula the LDA solution over a period of 15 min. The reaction mixture was stirred for an additional 40 minutes. Then a solution of nitroethylene (1.45 g, 20.53 mmol) in dry THF (20 mL) was added dropwise via cannula to the reaction mixture over a period of 15 min. After stirring for 2 h at −78° C., the reaction was quenched by adding a saturated solution of ammonium chloride (20 mL). It was extracted with ethyl acetate (5×25 mL), dried ($Na_2SO_4$), filtered and concentrated by rotary evaporation to give 3.82 g of the desired product (86% pure) as a light brown liquid, which was taken on to the next step without further purification.

2'H-spiro[azabicyclo[2.2.1]heptane-2,3'-pyrrolidin]-2'-one

Ethyl 1-aza-2-(nitroethyl)bicyclo[2.2.1]heptane-2-carboxylate (3.82 g, 86% pure, 15.78 mmol) was dissolved in ethanol (50 mL) in a hydrogenolysis bottle. A catalytic amount of Raney nickel was added and the mixture was subjected to hydrogenolysis at 50 psi on a Parr apparatus for 16 h. The catalyst was removed by filtration through a celite plug and washed with ethanol (20 mL). A catalytic amount (5 mg) of p-toluenesulfonic acid was added and the reaction mixture was refluxed for 12 h. The solvent was removed by rotary evaporation to afford a light brown solid. This was dissolved in conc. $NaHCO_3$ solution (10 mL), saturated with NaCl and extracted with chloroform (4×40 mL). The combined chloroform extracts were dried ($K_2CO_3$), filtered and concentrated by rotary evaporation to give a light brown solid. It was purified by column chromatography, using $MeOH:CHCl_3:NH_4OH$ (9:1:0.01, v/v) as the eluent, to afford 1.96 g (75%) of 2'H-spiro[azabicyclo[2.2.1]heptane-2,3'-pyrrolidin]-2'-one as a cream-colored solid (m.p. 98° C.).

Spiro[1-azabicyclo[2.2.1]heptane-2,3'-pyrrolidine]

To a solution of 2'H-spiro[azabicyclo[2.2.1]heptane-2,3'-pyrrolidin]-2'-one (1.00 g, 6.02 mmol) in dry THF (20 mL) at 0° C. under $N_2$ atmosphere was added lithium aluminum hydride (647 mg, 17.7 mmol) and the mixture was refluxed for 24 h. The reaction mixture was cooled in ice bath and then ether (20 mL) was added. Excess hydride was quenched by the dropwise addition of 5 M solution of NaOH. The resulting solid aluminate salts were removed by filtration through a celite plug. The filtrate was dried ($Na_2SO_4$), filtered and concentrated by rotary evaporation to yield 800 mg of spiro[1-azabicyclo[2.2.1]heptane-2,3'-pyrrolidine] as a colorless liquid (87.43%).

1'-(3-Pyridyl)-spiro[1-azabicyclo[2.2.1]heptane-2,3'-pyrrolidine]Dihydrochloride A mixture of spiro[1-azabicyclo[2.2.1]heptane-2,3'-pyrrolidine] (300 mg, 1.98 mmol), 3-bromopyridine (344 mg, 2.18 mmol), tris(dibenzylideneacetone)dipalladium(0) (54.57 mg, 0.0654 mmol), rac-2,2'-bis(diphenylphosphino)-1,1'-binaphthyl (74.22 mg, 0.131 mmol) and potassium tert-butoxide (668.8 mg, 5.96 mmol) in dry toluene (20 mL) was heated in a sealed tube flushed with argon gas at 90° C. for 8 h. The reaction was cooled to 0° C. and the contents transferred to a 100 mL round bottom flask. The solvent was removed by rotary evaporation and the residue was dissolved in a saturated solution of $NaHCO_3$ (10 mL) and extracted with chloroform (4×15 mL). The combined chloroform extracts were dried ($K_2CO_3$), filtered and concentrated by rotary evaporation to give a dark colored syrup. This was purified by column chromatography, using $MeOH:CHCl_3:NH_4OH$ (8:2:0.01, v/v) as the eluent, to afford 350 mg (79.0%) of 1'-(3-pyridyl)-spiro[1-azabicyclo[2.2.1]heptane-2,3'-pyrrolidine] as a light brown syrup. A portion of the free base (200 mg) was converted to a hydrochloride salt, which was crystallized from isopropanol and ethanol to yield 200 mg (76%) of a light brown solid, (m.p. 232°–236° C.).

EXAMPLE 7

Sample 7 is 1'-(5-ethoxy-3-pyridyl)-spiro[1-azabicyclo[2.2.1]heptane-2,3'-pyrrolidine], which was prepared according to the following techniques:

1'-(5-Ethoxy-3-pyridyl)-spiro[1-azabicyclo[2.2.1]heptane-2,3'-pyrrolidine]

A mixture of spiro[1-azabicyclo[2.2.1]heptane-2,3'-pyrrolidine] (50 mg, 0.3 mmol) tris(dibenzylideneacetone) dipalladium(0) (9 mg, 0.009 mmol), rac-2,2'-bis(diphenylphosphino)-1,1'-binaphthyl (12 mg, 0.018 mmol), potassium tert-butoxide (147 mg, 1.2 mmol), and 5-bromo-3-ethoxypyridine (73 mg, 0.36 mmol) in dry toluene (5 mL) was placed in a sealed tube under argon and heated at 160° C. for 17 h. The reaction was cooled to 0° C. and the contents transferred to a 100 mL round bottom flask. The solvent was removed by rotary evaporation and the residue was dissolved in a saturated solution of $NaHCO_3$ (10 mL) and extracted with chloroform (4×15 mL). The combined chloroform extracts were dried ($K_2CO_3$), filtered and concentrated by rotary evaporation to give a dark colored syrup. This was purified by column chromatography, using $MeOH:CHCl_3:NH_4OH$ (8:2:0.01, v/v) as the eluent, to give 28 mg (27%) of 1'-(5-ethoxy-3-pyridyl)-spiro[1-azabicyclo[2.2.1]heptane-2,3'-pyrrolidine] as a viscous brown oil.

EXAMPLE 8

Sample 8 is 1'-(5-phenoxy-3-pyridyl)-spiro[1-azabicyclo[2.2.1]heptane-2,3'-pyrrolidine], which was prepared according to the following techniques:

1'-(5-Phenoxy-3-pyridyl)-spiro 1'-azabicyclo[2.2.1]heptane-2,3'-pyrrolidine]

A mixture of spiro[1-azabicyclo[2.2.1]heptane-2,3'-pyrrolidine] (50 mg, 0.3 mmol), tris(dibenzylideneacetone) dipalladium(0) (9 mg, 0.009 mmol), rac-2,2'-bis(diphenylphosphino)-1,1'-binaphthyl (12 mg, 0.018 mmol), potassium tert-butoxide (147 mg, 1.3 mmol), and 5-bromo-3-phenoxypyridine (90 mg, 0.36 mmol) in dry toluene (5 mL) was heated in a sealed tube under argon at 160° C. for 17 h. The reaction was cooled to 0° C. and the contents transferred to a 100 mL round bottom flask. The solvent was removed by rotary evaporation and the residue was dissolved in a saturated solution of $NaHCO_3$ (10 mL) and extracted with chloroform (4×15 mL). The combined chloroform extracts were dried ($K_2CO_3$), filtered and concentrated by rotary evaporation to give a dark colored syrup. This was purified by column chromatography, using $MeOH:CHCl_3:NH_4OH$ (8:2:0.01, v/v) as the eluent, to afford 55.8 mg of 1'-(5-phenoxy-3-pyridyl)-spiro[1-azabicyclo[2.2.1]heptane-2,3'-pyrrolidine] (52%) as a viscous tan oil.

EXAMPLE 9

Sample 9 is 1'-(5-pyrimidinyl)-spiro[1-azabicyclo[2.2.1]heptane-2,3'-pyrrolidine], which was prepared according to the following techniques:

1'-(5-Pyrimidinyl)-spiro[1-azabicyclo[2.2.1]heptane-2,3'-pyrrolidine]

A mixture of spiro[1-azabicyclo[2.2.1]heptane-2,3'-pyrrolidine] (100 mg, 0.06 mmol), tris(dibenzylideneacetone)dipalladium(0) (18 mg, 0.0018 mmol), rac-2,2'-bis(diphenylphosphino)-1,1'-binaphthyl (24 mg, 0.0036 mmol), potassium tert-butoxide (300 mg, 2.6 mmol), and 5-bromopyrimidine (114 mg, 0.7 mmol) in dry toluene (10 mL) was placed in a sealed tube under argon and heated at 125° C. for 17 h. The reaction was cooled to 0° C. and the contents transferred to a 100 mL round bottom flask.

The solvent was removed by rotary evaporation and the residue was dissolved in a saturated solution of NaHCO₃ (10 mL) and extracted with chloroform (4×15 mL). The combined chloroform extracts were dried (K₂CO₃), filtered and concentrated by rotary evaporation to give a dark colored syrup. This was purified by column chromatography, using MeOH:CHCl₃:NH₄OH (8:2:0.01, v/v) as the eluent, to afford 49.0 mg of 1'-(5-pyrimidinyl)-spiro[1-azabicyclo[2.2.1]heptane-2,3'-pyrrolidine] (32%) as a viscous brown oil.

EXAMPLE 10

Sample 10 is 1'-(3-pyridyl)-spiro[1-azabicyclo[2.2.2]octane-2,3'-pyrrolidine], which was prepared according to the following techniques:
Ethyl quinuclidine-2-carboxylate The ethyl quinuclidine-2-carboxylate for this synthesis was prepared according to the method described by Ricciardi and Doukas (*Heterocycles* 24:971 (1986)). We have also prepared ethyl quinuclidine-2-carboxylate using chemistry analogous to that used for the synthesis of ethyl 1-azabicyclo[2.2.1]heptane-2-carboxylate, but using 4-(bromomethyl)oxane in place of 3-(bromomethyl)oxolane.
Ethyl 2-(2-nitroethyl)quinuclidine-2-carboxylate Lithium diisopropylamide was prepared at 0° C. from lithium diisopropylamine (193.53 mg, 1.91 mmol) and n-butyllithium (0.764 mL, 1.91 mmol) under N₂. It was added via cannula to a stirring solution of ethyl quinuclidine-2-carboxylate (320 mg, 1.74 mmol) in dry THF (10 mL) at −78° C. After 1 h, a solution of nitroethylene (140.41 mg, 1.91 mmol) in THF (5 mL) was added dropwise to the reaction mixture. After stirring for 2 h at −78° C., the reaction was quenched by adding a saturated solution of ammonium chloride (20 mL). It was extracted with ethyl acetate (5×25 mL), dried (Na₂SO₄), filtered and concentrated by rotary evaporation to give 325 mg (70% pure) ethyl 2-(2-nitroethyl)quinuclidine-2-carboxylate as a light brown liquid, which was taken on to the next step without further purification.
2'H-spiro[azabicyclo[2.2.2]octane-2,3'-pyrrolidin]-2'-one A solution of ethyl 2-(2-nitroethyl)quinuclidine-2-carboxylate (320 mg,) in ethanol (10 mL) was subjected to hydrogenolysis at 50 psi on a Parr apparatus for 16 h using Raney nickel as a catalyst. The catalyst was removed by filtration through a celite plug and washed with ethanol (20 mL). A catalytic amount (5 mg) of p-toluenesulfonic acid was added and the reaction mixture was refluxed for 12 h. The solvent was removed by rotary evaporation to afford a light brown solid. This was dissolved in conc. NaHCO₃ solution (10 mL), saturated with NaCl and extracted with chloroform (4×40 mL). The combined chloroform extracts were dried (K₂CO₃), filtered and concentrated by rotary evaporation to give a light brown solid. It was purified by chromatography, using MeOH:CHCl₃:NH₄OH (8:2:0.01, v/v) as the eluent, to give 120 mg (38.2%) of desired compound as light cream-colored solid (m.p. 103°–105° C.).
Spiro[1-azabicyclo[2.2.2] octane-2,3'-pyrrolidine]

To a solution of 2'H-spiro[azabicyclo[2.2.2]octane-2,3'-pyrrolidin]-2'-one (100 mg, 0.55 mmol) in dry THF (10 mL) at 0° C. under N₂ atmosphere was added lithium aluminum hydride (74 mg, 1.94 mmol) and the mixture was refluxed for 24 h. The reaction mixture was cooled in ice bath and then ether (20 mL) was added. Excess hydride was quenched by the dropwise addition of 5 M solution of NaOH. The resulting solid aluminate salts were removed by filtration through a celite plug. The filtrate was dried (Na₂SO₄), filtered and concentrated by rotary evaporation to yield 83 mg of spiro[1-azabicyclo[2.2.2]octane-2,3'-pyrrolidine] as a colorless liquid (90%).

1'-(3-Pyridyl)-spiro[1-azabicyclo[2.2.2]octane-2,3'-pyrrolidine]

A stirring solution of spiro[1-azabicyclo[2.2.2]octane-2,3'-pyrrolidine] (80 mg, 0.48 mmol), tris(dibenzylidineacetone)dipalladium(0) (26.47 mg, 0.024 mmol), rac-2,2'-bis(diphenylphosphino)-1,1'-binaphthyl (30 mg, 0.048 mmol) and potassium tert-butoxide (215 mg, 1.92 mmol) in dry toluene (15 mL) was placed in a sealed tube under argon and heated at 90° C. for 16 h. The reaction was cooled to 0° C. and the contents transferred to a 100 mL round bottom flask. The solvent was removed by rotary evaporation and the residue was dissolved in a saturated solution of NaHCO₃ (10 mL) and extracted with chloroform (4×15 mL). The combined chloroform extracts were dried (K₂CO₃), filtered and concentrated by rotary evaporation to give a dark colored syrup. This was purified by column chromatography, using MeOH:CHCl₃:NH₄OH (8:2:0.01, v/v) as the eluent, to give 102 mg (85.7%) of 1'-(3-pyridyl)-spiro[1-azabicyclo[2.2.2]octane-2,3'-pyrrolidine] as a light brown syrup.

EXAMPLE 11

Sample 11 is 1'-(3-pyridyl)-2'H-spiro[1-azabicyclo[2.2.1]heptane-7,3'-pyrrolidine], which was prepared according to the following techniques:
Ethyl 2-(2H,3H,5H4-oxinyl)-2-nitroacetate A 2 M solution of titanium tetrachloride in THF was made by slow addition of the titanium tetrachloride (7.59 g, 40 mmol) to dry THF (20 mL) at 0° C. under an nitrogen. atmosphere. Ethyl nitroacetate (2.66 g, 20 mmol) was then added to the stirring solution, and the mixture was stirred for 5 min. Next, tetrahydro-4-H-pyran-4-one (2.00 g, 20 mmol) was added in one portion. Then, a 1.0 M solution of N-methyl morpholine in THF (8.09 g, 80 mmol) was added dropwise over a period of 2 h at 0° C. The mixture was then allowed to warm to room temperature and was stirred for 18 h. It was then poured into water (20 mL) and extracted with ethyl acetate (5×40 mL). The combined extracts were dried over Na₂SO₄, filtered and concentrated by rotary evaporation. The thick brown syrup was purified by column chromatography, using ethyl acetate:hexane (1:9, v/v) as eluent, to afford 3.00 g of pure compound as a light-brown syrup (70%).
Ethyl 2-(4-oxanyl)-2-aminoacetate Raney nickel (~2 g) was added to a solution of ethyl 2-(2H,3H,5H-4-oxinyl)-2-nitroacetate (2.50 g, 11.62 mmol) in ethanol (50 mL) and conc. HCl (1 mL). The mixture was subjected to hydrogenolysis at 50 psi on a Parr apparatus for 18 h. The catalyst was removed by careful filtration through a celite plug. The solvent was removed by rotary evaporation. The residue was basified with saturated aqueous NaHCO₃ to pH 8–9, then saturated with NaCl and extracted with chloroform (4×25 mL). The combined extracts were dried over K₂CO₃, filtered and concentrated to yield 2.40 g (~100%) of desired compound as a tan liquid.
1-azabicyclo[2.2.1]heptane-7-carboxylic acid hydrochloride Ethyl 2-(oxanyl)-2-aminoacetate (1.50 g, 8.02 mmol) was dissolved in 48% HBr (10 mL) in a pressure tube and saturated with HBr gas. The tube was sealed carefully and heated for 12 h at 120°–130° C. The reaction was cooled to room temperature, transferred to a 250 mL round bottom flask, and the acid was removed by rotary evaporation. The dark colored residue was dissolved in 30% ammonia solution (50 mL). This mixture was stirred for 5 h at room temperature, until cyclization to the desired acid was complete. The ammonia solution was removed by rotary evaporation to afford a light brown solid, which was redissolved in 5 mL of water and purified on an ion exchange resin using water as the eluent and ammonia (30% aq.). Ammoniacal fractions containing the desired acid were combined and concentrated to afford pure acid, which was converted to an HCl salt and crystallized from isopropanol and diethyl ether to give 1.21 g (85%) of a cream-colored solid (m.p. 232° turns brown, melts at 253°–254° C.).

Ethyl 1-azabicyclo[2.2.1]heptane-7-carboxylate

A solution of 1-azabicyclo[2.2.1]heptane-7-carboxylic acid hydrochloride (1.20 g, 6.76 mmol) in absolute ethanol (10 mL) and concentrated sulfuric acid (2 mL) was refluxed for 8 h. The reaction mixture was cooled and then basified with saturated aqueous $NaHCO_3$ to pH 8–9. The solution was saturated with solid NaCl and extracted with chloroform (4×20 mL). The combined chloroform extracts were dried over $Na_2SO_4$, filtered and concentrated by rotary evaporation to give a light brown liquid. This was purified by Kugelrohr distillation at 120° C. and 2.5 mm pressure to afford 1.00 g (90%) as a colorless liquid.

Ethyl 1-aza-7-(2-nitroethyl)bicyclo[2.2.11 heptane-7-carboxylate

Lithium diisopropylamide was prepared by the addition of n-butyllithium (1.70 mL, 6.26 mmol) to diisopropylamine (431.1 mg, 6.26 mmol) in dry THF (5 mL) at 0° under a $N_2$ atmosphere. The reaction was stirred at room temperature for 15 min and then transferred via cannula to a stirring solution of ethyl 1-azabicyclo[2.2.1]heptane-7-carboxylate (600 mg, 3.55 mmol) in THF (20 mL) at –78° C. under a $N_2$ atmosphere. The reaction mixture was stirred for 30 min at –78° C., then a solution of nitroethylene (285.3 mg, 3.91 mmol) in THF (10 mL) was added via cannula and the reaction was stirred for additional 2 h at –78° C. Then the reaction was quenched with saturated $NH_4Cl$ solution (10 mL). The reaction mixture was allowed to warm to room temperature and then was extracted with ethyl acetate (4×20 mL). The combined fractions were dried ($K_2CO_3$), filtered and concentrated by rotary evaporation to give 650 mg of a light-brown liquid. It was purified by column chromatography, using ethyl acetate:dichloromethane (8:2, v/v), to give 600 mg (85%) of tan liquid.

2'H-Spiro[1-azabicyclo[2.2.1]heptane-7,3'-pyrrolidin]-2'-one

Ethyl 1-aza-7-(2-nitroethyl)bicyclo[2.2.1]heptane-7-carboxylate (550 mg, 2.27 mmol) was dissolved in ethanol (25 mL) and subjected to hydrogenolysis at 50 psi for 18 h, using Raney nickel as a catalyst. The catalyst was removed by filtration through a celite plug. The solvent was removed by rotary evaporation. The resultant residue was dissolved in toluene (50 mL) and a catalytic amount of p-toluenesulfonic acid (10 mg) was added. The solution was refluxed for 12 h and then the solvent was removed by rotary evaporation. The residue was added to saturated $NaHCO_3$ (10 mL) solution and extracted with chloroform (5×15 mL). The combined chloroform extracts were dried ($K_2CO_3$), filtered, and concentrated. The residue was purified by column chromatography, using $CHCl_3$:MeOH:$NH_4OH$ (9:1:0.01, v/v) as the eluent, to afford 320 mg (85%) of pure compound as a cream-colored thick syrup.

2'H-Spiro 11-azabicyclo[2.2.1]heptane-7,3'-pyrrolidine]

To a stirring solution of 2'H-spiro[1-azabicyclo[2.2.1] heptane-7,3'-pyrrolidin]-2'-one (300 mg, 1.80 mmol) in dry THF (30 mL) at 0° under $N_2$ was added $LiAlH_4$ (274.33 mg, 7.22 mmol). The ice bath was removed and the reaction mixture was refluxed for 24 h. The reaction mixture was cooled to 0° C., diethyl ether (20 mL) was added and 5M NaOH was added dropwise with constant stirring until all unreacted $LiAlH_4$ solidified. The reaction mixture was filtered through celite and then the filtrate was dried ($K_2CO_3$), filtered and concentrated by rotary evaporation to yield 250 mg (70%) of a colorless syrup.

1'-(3-Pyridyl)-2'H-spiro[1-azabicyclo[2.2.1]heptane-7,3'-pyrrolidine]

2'H-Spiro[1-azabicyclo[2.2.1]heptane-7,3'-pyrrolidine] (100 mg, 0.66 mmol), tris(dibenzylideneacetone)dipalladium(0) (30 mg, 0.020 mmol), rac-2,2'-bis (diphenylphosphino)-1,1'-binaphthyl (45 mg, 0.040 mmol), potassium tert-butoxide (369 mg, 3.3 mmol) and 3-bromopyridine (114 mg, 0.72 mmol) and dry toluene (10 mL) were placed in a pressure tube which was flushed with argon. The tube was carefully sealed and heated for 8 h at 90° C. The reaction mixture was cooled, transferred to a round bottom flask and the solvent removed by rotary evaporation. The residue was poured into saturated $NaHCO_3$ solution (5 mL) and extracted with chloroform (4×15 mL). The combined chloroform extracts were dried over $K_2CO_3$, filtered and concentrated by rotary evaporation. The residue was purified by column chromatography, using $CHCl_3$:MeOH:$NH_4OH$ (8:2:0.01, v/v) as eluent, to afford 130 mg (86.7%) of a light brown syrup. The product turns dark brown on exposure to light and air.

EXAMPLES 12 AND 13

Samples 12 and 13 are (+) and (–) 7-(3-pyridyl)-1,7-diazaspiro[4.4]nonane respectively, which were prepared according to the following techniques:

Diastereomeric 7-(3-pyridyl)-1,7-diazaspiro[4.4]nonane S-proline Amides

Triethylamine (6.0 mL, 43 mmol) and diphenyl chlorophosphate (4.0 mL, 19 mmol) were added, in that order, to a stirred suspension of N-(tert-butoxycarbonyl)-S-proline (4.67 g, 21.7 mmol) in dichloromethane (100 mL) under a nitrogen atmosphere. After stirring for 1.5 h at ambient temperature, the reaction mixture was treated with a solution of 7-(3-pyridyl)-1,7-diazaspiro[4.4]nonane (4.40 g, 21.6 mmol) in dichloromethane (10 mL). The mixture was stirred 3 days at ambient temperature. Sodium hydroxide solution (30 mL of 5 M) was then added. After stirring an additional hour, the mixture was poured into a separatory funnel with chloroform (30 mL) and water (30 mL). The mixture was shaken vigorously, and the layers were separated. The organic layer and a 30 mL chloroform extract of the aqueous layer were combined, dried ($MgSO_4$) and concentrated by rotrary evaporation. The residue (7.2 g) was dissolved in dichloromethane (100 mL) and conbined with trifluroacetic acid (50 mL). The mixture was stirred at ambient temperature for 1 h. The volatiles were evaporated, first by rotary evaporation and then on the vacuum pump. The residue was purified by preparative HLPC, using 10% acetonitrile, 0.1% trifluoroacetic acid in water as eluent. Selected fractions were combined and concentrated, leaving 3.13 g (79% yield) of the diastereomer which elutes at 11.4 min and 2.90 g (74% yield) of the diastereomer that elutes at 13.2 min, both as white foams (presumably mono trifluoroacetate salts).

(+) and (–) 7-(3-pyridyl)-1,7-diazaspiro[4.4]nonane

Each of the two diastereomeric S-proline amides was dissolved in dichloromethane (50 mL) and triethylamine (2–3 mL), and then combined with phenylisothiocyanate (1.73 g, 12.8 mmol for the earlier eluting diastereomer and 1.57 g, 11.6 mmol for the later eluting diastereomer). The two reactions were stirred at ambient temperature for 16 h, at which point thin layer chromatography indicated that the reactions were complete. The mixtures were concentrated by rotary evaporation, and each of the residues was taken up in dichloromethane (10 mL) and treated with trifluoroacetic acid (10 mL). These reactions were held at 50° C. for 16 h and concentrated to dryness. Column chromatography on silica gel with 80:20:2 chlorform/methanol/ammonia gave 620 mg (derived from the earlier eluting diastereomer, 40.5% yield) and 720 mg (derived from the later eluting diastereomer, 50.7% yield), as light brown oils. Chiral HPLC analysis was perormed on a Chiralcel OD® column, using 7:3 heaxane/ethanol. The isomer derived from the earlier eluting diastereomer had the longer retention time on the chiral column (10.9 min); that derived from the later eluting isomer exhibited a retention time of 8.7 min on the chiral column. The samples were enantiomerically pure within the limits of detection (~2%).

Having hereby disclosed the subject matter of the present invention, it should be apparent that many modifications, substitutions, and variations of the present invention are possible in light thereof. It is to be understood that the present invention can be practiced other than as specifically described. Such modifications, substitutions and variations are intended to be within the scope of the present application.

What is claimed is:

1. A diazaspiro nonane compound having the following formula:

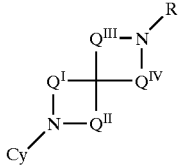

Formula 1 and pharmaceutically acceptable salts thereof,
wherein $Q^I$ is $(CZ_2)_u$, $Q^{II}$ is $(CZ_2)_v$, $Q^{III}$ is $(CZ_2)_w$, and $Q^{IV}$ is $(CZ_2)_x$,
u, v, w and x are individually 0, 1, 2, 3 or 4, preferably 0, 1, 2 or 3,
and the values of u, v, w and x are selected such that the ring is a diazaspiro nonane,
R is hydrogen, lower alkyl, acyl, alkoxycarbonyl or aryloxycarbonyl,
Z is, individually, selected from the group consisting of hydrogen, alkyl, substituted alkyl, cycloalkyl, substituted cycloalkyl, aryl, substituted aryl, alkylaryl, substituted alkylaryl, arylalkyl and substituted arylalkyl;
Cy is a six membered ring of the formula:

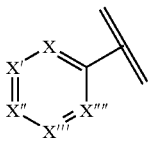

where one of X, X', X", X'" and X"" is nitrogen, and the others are carbon bonded to a substituent species,
wherein "substituent species" are, individually, selected from the group consisting of hydrogen, alkyl, substituted alkyl, alkenyl, substituted alkenyl, cycloalkyl, substituted cycloalkyl, aryl, substituted aryl, alkylaryl, substituted alkylaryl, arylalkyl, substituted arylalkyl, halo, —OR', —NR'R", —$CF_3$, —CN, —$NO_2$, —$C_2R'$, —SR', —$N_3$, —C(=O)NR'R", —NR'C(=O)R", —C(=O)R', —C(=O)OR', —OC(=O)R', —O(CR'R")$_1$C(=O)R', —O(CR'R")$_r$NR"C(=O)R', —O(CR'R")$_r$NR"$SO_2$R', —OC(=O)NR'R", —NR'C(=O)O R", —$SO_2$R', —$SO_2$NR'R", and —NR'$SO_2$R",
where R' and R" are individually hydrogen, $C_1$–$C_8$ alkyl, cycloalkyl, aryl, or arylalkyl, and r is an integer from 1 to 6, or R' and R" can combine to form a cyclic functionality, and
wherein "substituted" as applied to alkyl, aryl, cycloalkyl and the like refers to the substituents described above, starting with halo and ending with —NR'$SO_2$R".

2. The compound of claim 1, wherein X'" is nitrogen.
3. The compound of claim 1, wherein X, X" and X"" are carbon bonded to a substituent species.
4. The compound of claim 3, where the substituent species at X, X" and X"" are hydrogen.
5. A pharmaceutical composition including a compound of claim 1 along with a pharmaceutically acceptable carrier.
6. A compound selected from the group consisting of:

7-(3-pyridyl)-1,7-diazaspiro[4.4]nonane
7-(5-methoxy-3-pyridyl)-1,7-diazaspiro[4.4]nonane
7-(5-cyclopentyloxy-3-pyridyl)-1,7-diazaspiro[4.4]nonane
7-(5-phenoxy-3-pyridyl)-1,7-diazaspiro[4.4]nonane
7-(5-(4-hydroxyphenoxy)-3-pyridyl)-1,7-diazaspiro[4.4]nonane
7-(5-ethynyl-3-pyridyl)-1,7-diazaspiro[4.4]nonane
7-(6-chloro-3-pyridyl)-1,7-diazaspiro[4.4]nonane
1-(3-pyridyl)-1,7-diazaspiro[4.4]nonane
1-methyl-7-(3pyridyl)-1,7-diazaspiro[4.4]nonane
1-methyl-7-(5-methoxy-3-pyridyl)-1,7-diazaspiro[4.4]nonane
1-methyl-7-(5-cyclopentyloxy-3-pyridyl)-1,7-diazaspiro[4.4]nonane
1-methyl-7-(5-phenoxy-3-pyridyl)-1,7-diazaspiro[4.4]nonane
1-methyl-7-(5-(4-hydroxyphenoxy)-3-pyridyl)-1,7-diazaspiro[4.4]nonane
1-methyl-7-(5-ethynyl-3-pyridyl)-1,7-diazaspiro[4.4]nonane
1-methyl-7-(6-chloro-3-pyridyl)-1,7-diazaspiro[4.4]nonane
7-methyl-1-(3-pyridyl)-1,7-diazaspiro[4.4]nonane
2-(3-pyridyl-2,7-diazaspiro[4.4]nonane
2-(5-methoxy-3-pyridyl)-2,7-diazaspiro[4.4]nonane
2-(5-cyclopentyloxy-3-pyridyl)-2,7-diazaspiro[4.4]nonane
2-(5-phenoxy-3-pyridyl)-2,7-diazaspiro[4.4]nonane
2-(5-(4-hydroxyphenoxy)-3-pyridyl)-2,7-diazaspiro[4.4]nonane
2-(5-ethynyl-3-pyridyl)-2,7-diazaspiro[4.4]nonane
2-(6-chloro-3-pyridyl)-2,7-diazaspiro[4.4]nonane
2-methyl-7-(3-pyridyl)-2,7-diazospiro[4.4]nonane
2-methyl-7-(5-methoxy-3-pyridyl)-2,7-diazospiro[4.4]nonane
2-methyl-7-(5-phenoxy-3-pyridyl)-2,7-diazospiro[4.4]nonane
6-(3-pyridyl)-1,6-diazaspiro[3.5]nonane
1-methyl-6-(3-pyridyl)-1,6-diazaspiro[3.5]nonane
2-(3-pyridyl)-2,5-diazaspiro[3.5]nonane
5-methyl-2-(3-pyridyl)-2,5-diazaspiro[3.5]nonane and
pharmaceutically acceptable salts thereof.

7. A pharmaceutically composition comprising an effective amount of a compound of claim 6 along with a pharmaceutically acceptable carrier.

* * * * *

UNITED STATES PATENT AND TRADEMARK OFFICE
CERTIFICATE OF CORRECTION

PATENT NO. : 6,956,042 B2
APPLICATION NO. : 10/607930
DATED : October 18, 2005
INVENTOR(S) : Bhatti et al.

It is certified that error appears in the above-identified patent and that said Letters Patent is hereby corrected as shown below:

Title page, item 56, under the Foreign Patent Document, Col. 2, right-handed should be corrected as follows:

--WO 01/66546 A1  9/2001--

Claim 6, Column 46, Line 39 should read --2-(3-pyridyl)-2,7-diazaspiro[4.4]nonane.--

Signed and Sealed this

Sixth Day of March, 2007

JON W. DUDAS
*Director of the United States Patent and Trademark Office*

UNITED STATES PATENT AND TRADEMARK OFFICE
CERTIFICATE OF CORRECTION

PATENT NO. : 6,956,042 B2
APPLICATION NO. : 10/607930
DATED : October 18, 2005
INVENTOR(S) : Bhatti et al.

It is certified that error appears in the above-identified patent and that said Letters Patent is hereby corrected as shown below:

In the Title:

Item [54] in the Title on the face page of the patent and Column 1, Line 1, "DIAZASPIRACYCLIC" should be replaced with -- DIAZASPIROCYCLIC --

In the Claims:

Col. 45, in Claim 1, line 24, replace "and pharmaceutically acceptable salts thereof," with -- or a pharmaceutically acceptable salt thereof, --

Col. 46, in Claim 6, line 60, add -- and -- after "nonane"

Col. 46, in Claim 6, line 61, replace "and pharmaceutically acceptable salts thereof." with -- or a pharmaceutically acceptable salt thereof. --

Signed and Sealed this

Twenty-ninth Day of July, 2008

JON W. DUDAS
*Director of the United States Patent and Trademark Office*